US009277954B2

(12) United States Patent
Germain et al.

(10) Patent No.: US 9,277,954 B2
(45) Date of Patent: *Mar. 8, 2016

(54) MEDICAL ABLATION SYSTEM AND METHOD OF USE

(71) Applicant: ARQOS Surgical, Inc., Cupertino, CA (US)

(72) Inventors: Aaron Germain, Campbell, CA (US); Balazs Lesko, Budapest (HU); Benedek Orczy-Timko, Budapest (HU)

(73) Assignee: ARQOS Surgical, Inc., Cupertino, CA (US)

( * ) Notice: Subject to any disclaimer, the term of this patent is extended or adjusted under 35 U.S.C. 154(b) by 473 days.

This patent is subject to a terminal disclaimer.

(21) Appl. No.: 13/664,232

(22) Filed: Oct. 30, 2012

(65) Prior Publication Data

US 2013/0296849 A1 Nov. 7, 2013

Related U.S. Application Data

(63) Continuation of application No. 13/287,315, filed on Nov. 2, 2011, now Pat. No. 8,323,280.

(60) Provisional application No. 61/454,901, filed on Mar. 21, 2011, provisional application No. 61/491,541, filed on May 31, 2011, provisional application No. 61/537,483, filed on Sep. 21, 2011.

(51) Int. Cl.
*A61B 18/14* (2006.01)
*A61B 18/04* (2006.01)
*A61B 18/00* (2006.01)

(52) U.S. Cl.
CPC ..... *A61B 18/042* (2013.01); *A61B 2018/00565* (2013.01); *A61B 2018/00577* (2013.01)

(58) Field of Classification Search
CPC ................... A61B 18/042; A61B 2018/00565; A61B 2018/00577
See application file for complete search history.

(56) References Cited

U.S. PATENT DOCUMENTS

| 2,513,564 | A | 7/1950 | Ingwersen |
| 2,514,545 | A | 7/1950 | Ingwersen |
| 2,625,625 | A | 1/1953 | Ingwersen |
| 2,689,895 | A | 9/1954 | Ingwersen |
| 3,611,023 | A | 10/1971 | Souza, Jr. et al. |
| 3,838,242 | A * | 9/1974 | Goucher .................. 219/121.36 |
| 3,848,211 | A | 11/1974 | Russell |
| 3,868,614 | A | 2/1975 | Riendeau |

(Continued)

FOREIGN PATENT DOCUMENTS

| EP | 1034747 A1 | 9/2000 |
| WO | WO 00/53112 A2 | 9/2000 |

(Continued)

OTHER PUBLICATIONS

U.S. Appl. No. 13/369,983, filed Feb. 9, 2012, Truckai et al.

(Continued)

*Primary Examiner* — Michael Peffley
(74) *Attorney, Agent, or Firm* — Wilson Sonsini Goodrich & Rosati

(57) ABSTRACT

Cartilage and other tissues are treated by generating a plasma in an interior space of a probe and exposing the tissue to the plasma. The plasma is released through a gap in a working end of the probe.

24 Claims, 27 Drawing Sheets

(56) References Cited

U.S. PATENT DOCUMENTS

| | | | |
|---|---|---|---|
| 3,903,891 A | 9/1975 | Brayshaw | |
| 4,060,088 A | 11/1977 | Morrison, Jr. et al. | |
| 4,272,687 A | 6/1981 | Borkan | |
| 4,781,175 A * | 11/1988 | McGreevy et al. | 606/40 |
| 4,977,346 A | 12/1990 | Gibson et al. | |
| 5,012,495 A | 4/1991 | Munroe et al. | |
| 5,122,138 A | 6/1992 | Manwaring | |
| 5,207,675 A | 5/1993 | Canady | |
| 5,256,138 A | 10/1993 | Burek et al. | |
| 5,277,201 A | 1/1994 | Stern | |
| 5,281,217 A | 1/1994 | Edwards et al. | |
| 5,449,356 A | 9/1995 | Walbrink et al. | |
| 5,669,907 A | 9/1997 | Platt, Jr. et al. | |
| 5,683,366 A | 11/1997 | Eggers et al. | |
| 5,720,745 A * | 2/1998 | Farin et al. | 606/49 |
| 5,776,092 A | 7/1998 | Farin et al. | |
| 5,817,092 A | 10/1998 | Behl | |
| 5,849,010 A | 12/1998 | Wurzer et al. | |
| 5,873,855 A | 2/1999 | Eggers et al. | |
| 5,888,198 A | 3/1999 | Eggers et al. | |
| 5,891,095 A | 4/1999 | Eggers et al. | |
| 5,964,752 A | 10/1999 | Stone | |
| 5,989,248 A | 11/1999 | Tu et al. | |
| 6,013,075 A | 1/2000 | Avramenko et al. | |
| 6,013,076 A | 1/2000 | Goble et al. | |
| 6,024,733 A | 2/2000 | Eggers et al. | |
| 6,032,674 A | 3/2000 | Eggers et al. | |
| 6,039,736 A | 3/2000 | Platt, Jr. | |
| 6,056,747 A | 5/2000 | Saadat et al. | |
| 6,066,134 A | 5/2000 | Eggers et al. | |
| 6,080,152 A | 6/2000 | Nardella et al. | |
| 6,099,523 A * | 8/2000 | Kim et al. | 606/40 |
| 6,142,992 A | 11/2000 | Cheng et al. | |
| 6,149,620 A | 11/2000 | Baker et al. | |
| 6,159,208 A | 12/2000 | Hovda et al. | |
| 6,174,308 B1 | 1/2001 | Goble et al. | |
| 6,225,883 B1 | 5/2001 | Wellner et al. | |
| 6,235,020 B1 | 5/2001 | Cheng et al. | |
| 6,238,391 B1 | 5/2001 | Olsen et al. | |
| 6,296,636 B1 | 10/2001 | Cheng et al. | |
| 6,348,051 B1 * | 2/2002 | Farin et al. | 606/49 |
| 6,394,956 B1 | 5/2002 | Chandrasekaran et al. | |
| 6,413,256 B1 | 7/2002 | Truckai et al. | |
| 6,419,674 B1 | 7/2002 | Bowser et al. | |
| 6,443,948 B1 * | 9/2002 | Suslov | 606/40 |
| 6,475,215 B1 * | 11/2002 | Tanrisever | 606/45 |
| 6,538,549 B1 | 3/2003 | Renne et al. | |
| 6,579,289 B2 | 6/2003 | Schnitzler | |
| 6,632,220 B1 | 10/2003 | Eggers et al. | |
| 6,669,694 B2 * | 12/2003 | Shadduck | 606/41 |
| 6,720,856 B1 | 4/2004 | Pellon et al. | |
| 6,780,178 B2 | 8/2004 | Palanker et al. | |
| 6,821,275 B2 | 11/2004 | Truckai et al. | |
| 6,837,884 B2 | 1/2005 | Woloszko | |
| 6,890,332 B2 | 5/2005 | Truckai et al. | |
| 6,902,564 B2 | 6/2005 | Morgan et al. | |
| 7,087,054 B2 | 8/2006 | Truckai et al. | |
| 7,220,261 B2 | 5/2007 | Truckai et al. | |
| 7,309,849 B2 | 12/2007 | Truckai et al. | |
| 7,549,989 B2 | 6/2009 | Morgan et al. | |
| 7,713,269 B2 | 5/2010 | Auge, II et al. | |
| 7,744,595 B2 | 6/2010 | Truckai et al. | |
| 7,771,422 B2 | 8/2010 | Auge, II et al. | |
| 7,819,861 B2 | 10/2010 | Auge, II et al. | |
| 7,819,864 B2 | 10/2010 | Morgan et al. | |
| 7,955,331 B2 | 6/2011 | Truckai et al. | |
| 8,016,823 B2 * | 9/2011 | Shadduck | 606/41 |
| 8,075,555 B2 | 12/2011 | Truckai et al. | |
| 8,192,424 B2 | 6/2012 | Woloszko | |
| 8,192,428 B2 | 6/2012 | Truckai et al. | |
| 8,221,404 B2 | 7/2012 | Truckai | |
| 8,323,280 B2 | 12/2012 | Germain et al. | |
| 8,333,763 B2 | 12/2012 | Truckai et al. | |
| 2002/0087208 A1 | 7/2002 | Koblish et al. | |
| 2003/0014051 A1 | 1/2003 | Woloszko | |
| 2003/0125727 A1 | 7/2003 | Truckai et al. | |
| 2004/0044341 A1 | 3/2004 | Truckai et al. | |
| 2005/0075630 A1 | 4/2005 | Truckai et al. | |
| 2005/0228372 A1 | 10/2005 | Truckai et al. | |
| 2006/0058782 A1 | 3/2006 | Truckai et al. | |
| 2006/0224154 A1 | 10/2006 | Shadduck et al. | |
| 2007/0213704 A1 | 9/2007 | Truckai et al. | |
| 2009/0076498 A1 | 3/2009 | Saadat et al. | |
| 2009/0270849 A1 | 10/2009 | Truckai et al. | |
| 2010/0100091 A1 | 4/2010 | Truckai | |
| 2012/0245580 A1 | 9/2012 | Germain et al. | |
| 2012/0330292 A1 | 12/2012 | Shadduck et al. | |
| 2013/0317493 A1 | 11/2013 | Truckai et al. | |

FOREIGN PATENT DOCUMENTS

| | | |
|---|---|---|
| WO | WO 00/62685 A1 | 10/2000 |
| WO | WO 00/53112 A3 | 12/2000 |

OTHER PUBLICATIONS

U.S. Appl. No. 13/680,972, filed Nov. 19, 2012, Truckai et al.
European search report dated Nov. 2, 2009 for EP Application No. 01967968.7.
Kim, et al. Optical feedbacksignal for ultra short pulse ablation of tissue. Appl. Surface Sci. 1998; 127-129:857-862.
International search report dated Jan. 14, 2002 for PCT/US2001/025409.
International search report and written opinion dated May 23, 2012 for PCT/US2012/023390.
Tucker et al. Histologic characteristics of electrosurgical injuries. J. Am. Assoc. Gyneco. Laproscopy. 1997; 4(2):857-862.
Notice of allowance dated Apr. 12, 2010 for U.S. Appl. No. 11/090,706.
Notice of allowance dated Jun. 14, 2012 for U.S. Appl. No. 11/649,377.
Notice of allowance dated Jul. 30, 2012 for U.S. Appl. No. 13/287,315.
Notice of allowance dated Aug. 11, 2004 for U.S. Appl. No. 10/135,135.
Notice of allowance dated Aug. 28, 2012 for U.S. Appl. No. 12/790,561.
Notice of allowance dated Sep. 9, 2004 for U.S. Appl. No. 10/135,135.
Notice of allowance dated Nov. 10, 2011 for U.S. Appl. No. 11/649,377.
Office action dated Mar. 20, 2012 for U.S. Appl. No. 13/287,115.
Office action dated Mar. 23, 2011 for U.S. Appl. No. 11/649,377.
Office action dated May 9, 2008 for U.S. Appl. No. 11/090,706.
Office action dated May 12, 2009 for U.S. Appl. No. 11/090,706.
Office action dated Jun. 8, 2012 for U.S. Appl. No. 12/790,561.
Office action dated Sep. 19, 2008 for U.S. Appl. No. 11/090,706.
Office action dated Oct. 6, 2009 for U.S. Appl. No. 11/090,706.
Office action dated Nov. 17, 2010 for U.S. Appl. No. 11/649,377.
Office action dated Dec. 10, 2014 for U.S. Appl. No. 13/680,972.
Office action dated Dec. 15, 2006 for U.S. Appl. No. 10/995,660.

* cited by examiner

MEDICAL ABLATION SYSTEM AND METHOD OF USE

CROSS-REFERENCE TO RELATED APPLICATIONS

This application claims is a continuation of U.S. patent application Ser. No. 13/287,315, filed Nov. 2, 2011, now U.S. Pat. No. 8,323,280, which claims the benefit of U.S. Provisional Application Nos. 61/454,901, filed on Mar. 21, 2011; 61/491,541, filed on May 31, 2011; and 61/537,483, filed on Sep. 21, 2011, the full disclosures of which are incorporated herein by reference.

FIELD OF THE INVENTION

This invention relates to medical instruments and systems for applying energy to tissue, and more particularly relates to a system for ablating and treating damaged cartilage tissue.

BACKGROUND OF THE INVENTION

Various types of medical instruments utilizing radiofrequency (RF) energy, laser energy and the like have been developed for delivering thermal energy to tissue, for example to ablate tissue. While such prior art forms of energy delivery work well for some applications, prior art RF and laser devices are not capable of ablating surfaces of cartilage to provide smooth surfaces. Further, such prior art devices cause unacceptable thermal damage to cartilage tissue.

What is needed are systems and methods that can controllably apply energy to fibrillated or damaged cartilage to smooth the cartilage without any thermal damage to the cartilage surface layers.

SUMMARY OF THE INVENTION

A probe for ablating tissue comprises an electrosurgical working end comprising first and second dielectric bodies and defining an interior chamber, wherein an interface between the first and second bodies is sufficiently fluid-tight to prevent liquid flow therethrough but permit plasma propagation therethrough, first and second opposing polarity electrodes configured for creating a current path within the interface. A probe for cutting and extracting tissue, comprises an elongated introducer with a first channel for tissue-extraction having a termination in a working end surface, a second channel for plasma generation having a termination in the working surface, first and second polarity electrodes configured for igniting a plasma in a region of the second channel, and a negative pressure source in communication with the first and second channels. A method of ablating tissue, comprises providing an electrosurgical working end with an interior chamber communicating with a working surface through a space that is sufficiently fluid-tight to prevent liquid flow therethrough but permit plasma propagation therethrough, igniting a plasma in or adjacent to the gap utilizing first and second opposing polarity electrodes positioned on either side of the gap, and controlling propagation of the plasma through the gap to interface with tissue.

Methods for treating a target tissue utilize a probe having an interior space and a working end with a working surface. A plasma is ignited within the interior space and propagates outwardly from the working surface. The target tissue is exposed to the plasma for treatment, typically ablation, cutting, coagulation, resurfacing, tissue smoothing or the like.

In a first aspect of the present invention, the plasma is released from the interior space through a gap in the working end of the probe. Typically, a flow of saline or other conductive media is provided adjacent to or through the gap and ignited either before entering the gap or as it passes through the gap to generate the plasma. The gap typically has an interior periphery and an exterior periphery with a spacing therebetween which is sufficiently fluid tight (resistive to fluid flow) to inhibit fluid flow but permit plasma propagation there through. The plasma is typically ignited by applying electrical energy to the conductive medium from opposite polarity electrodes positioned on either side of the gap within one electrode within the interior space. For example, a first polarity electrode may be disposed in proximity to the inner-periphery of the gap or may be disposed in a fluid channel in communication with said inner-periphery. The second polarity electrode may be in or on the working end in potential fluid communication with the exterior periphery of the gap. The gap typically has a mean dimension (spacing) between said interior and exterior peripheries in the range from 0.005 inches to 0.25 inches. The total area of the gap surfaces may be in the range from 0.01 mm$^2$ to 10 mm$^2$. The gap may have any one of a variety of configurations, including annular, linear, oval, elongated, star shaped, and the like.

Methods of the present invention may further comprise controlling a rate of propagation of the plasma through the gap. The plasma propagation rate may be controlled by controlling a dimension of the gap, typically a width of the gap. Alternatively or additionally, the propagation rate may be controlled by controlling a dimension of the gap between a plasma initiation region within the interior space and the working surface. Still further alternatively or additionally, the propagation rate may be controlled by varying a pressure of the conductive media in the interior space, either by controlling the inlet pressure and/or an outlet pressure of the conductive media as it flows though the interior space.

In still other embodiments, igniting the plasma may comprise establishing a continuous "loop" flow of the conductive media throughout the interior space. In such embodiments, a portion of the conductive media is then ignited within the interior space and a remainder of the conductive medium exits the interior space. Typically, the conductive media enters the interior space through an inlet flow channel in the probe while the remainder of the conductive media exits through an outlet flow channel in the probe. The plasma which is generated within the interior space then exits or emerges through one or more gaps in the working end of the probe. In such embodiments, a propagation rate may be controlled by varying the inlet pressure, the outlet negative pressure, or a combination of both. The flows may also be controlled by varying a dimension of the gap. Plasmas are typically generated by passing current thorough opposite polarity electrodes in or near the interior space, and the interior space may comprise a channel transition zone between the inlet and outlet channels. Typically, the channel transition zone comprises a flow restriction, and the plasma is ignited at the flow restriction.

In all embodiments, the plasma typically propagates from the working surface by a distance of less than 2 mm, usually less than 1 mm, and often less than 0.5 mm. The temperature of the plasma will usually be less than 80° C., often less than 70° C., and frequently less than 60° C. Typically, the target tissue may be submerged in a conductive medium when it is being treated by the methods disclosed herein.

BRIEF DESCRIPTION OF THE DRAWINGS

FIG. 12A is a sectional view of an alternative working end similar to that of FIGS. 3-6, but configured with first and second polarity electrodes disposed in the interior of the working end, wherein FIG. 12A illustrates fluid flows within the device.

DETAILED DESCRIPTION OF THE INVENTION

Figure 1:
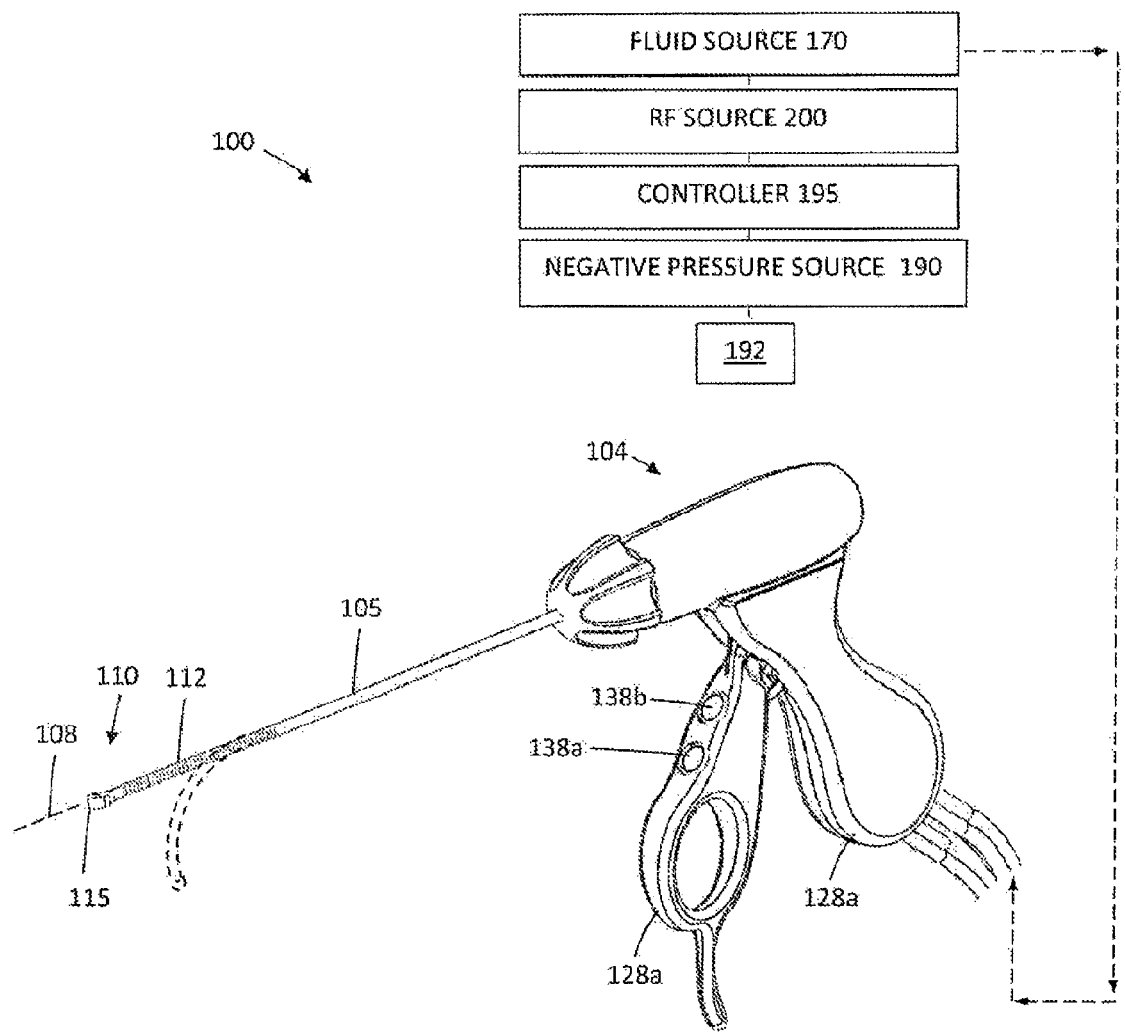
FIG. 1 is perspective view of the ablation device corresponding to the invention that includes an elongated shaft extending along an axis with an articulating working end.
Figure 2:
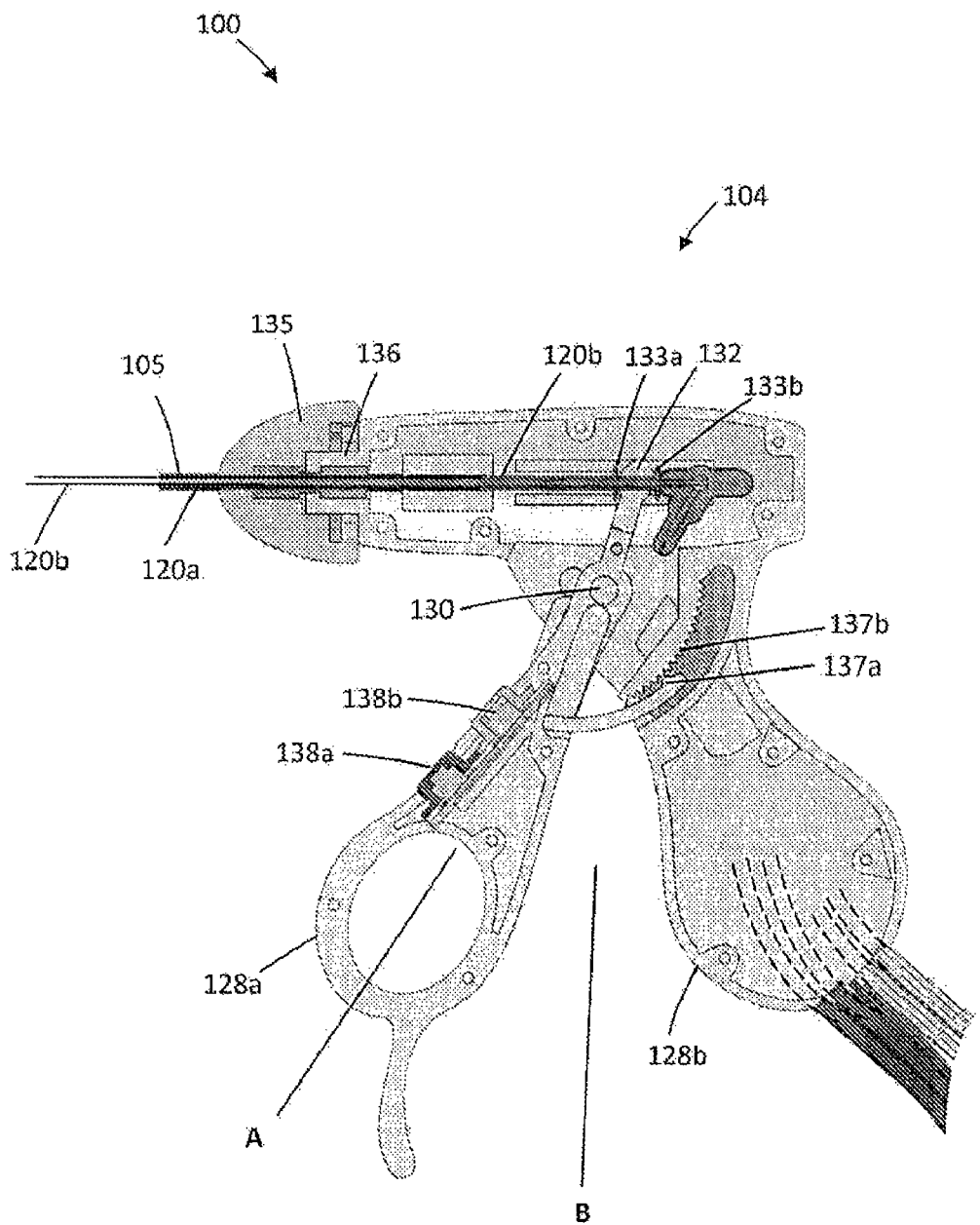
FIG. 2 is a sectional view of a handle portion of the device of FIG. 1.
Figure 3:
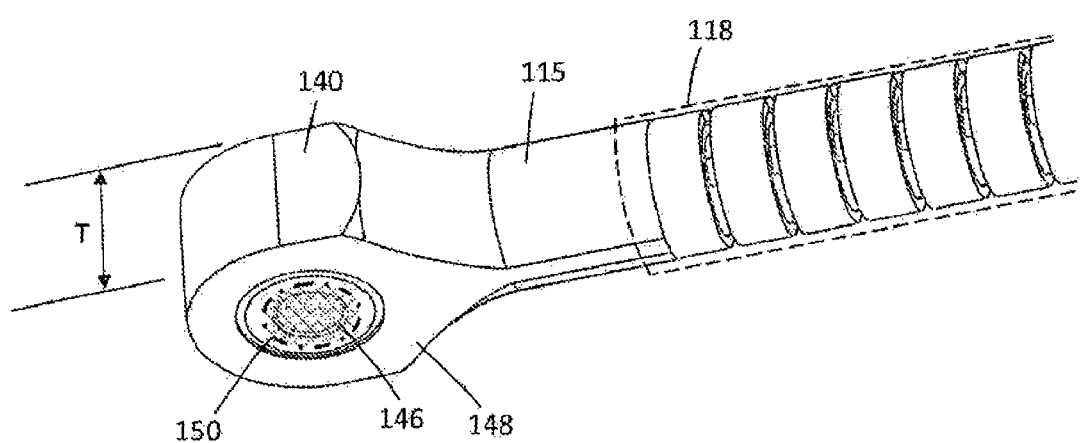
FIG. 3 is a perspective view of the distal ablation body portion of the device of FIG. 1.

Referring now to the drawings and the reference numbers marked thereon, FIGS. 1 and 2 illustrate one embodiment of chondroplasty plasma ablation device 100 that includes handle portion 104 and elongated shaft 105 that extends along longitudinal axis 108. The working end 110 comprises an articulating shaft portion 112 that allows the distal ablation body portion 115 to be articulated to 90° or more to thus allow the physician to orient the distal ablation body portion 115 as needed in a joint to ablate and smooth damaged regions of an articular surface, such as in a knee, hip, shoulder, ankle or other joint. In one embodiment, the shaft 105 comprises an assembly of concentric thin-wall inner and outer stainless steel sleeves 120a and 120b with an outermost assembly diameter of approximately 3.0 mm (FIGS. 2-3). An insulative polymer outer layer 118 is provided around the shaft 105, which can comprise a flexible temperature resistant material such as PEEK. It should be appreciated that the shaft 105 can be fabricated of a metal, polymer or combination thereof with a diameter ranging from about 1.0 mm to 6.0 mm. Referring to FIGS. 1, 3, 4 and 5A-5B, the articulating shaft portion 112 comprises inner and outer slotted sleeve portions, 122a and 122b, that are coupled at distal weld 124 to thus allow axial forces to be applied to one sleeve relative to the other sleeve to thus articulate the working end 110 as is known in the art. In the embodiment of FIGS. 1 and 2, the inner and outer slotted sleeve portions, 122a and 122b, can have any configuration of slot depth, orientation and shape to provide a desired range of articulated shapes, torque resistance and the like.

In FIG. 2, it can be seen that handle grip portion 128a can be moved toward handle portion 128b (from an 'open' position indicated at A toward a 'closed' position indicated at B) to articulate the working end 110. More in particular, the movement of handle portion 128a about pivot 130 causes the upper handle end block 132 to engage and move flanges 133a, 133b of the inner sleeve 120b distally to thus articulate the working end 110 between a linear shape and an articulated shape. FIGS. 1 and 2 illustrate that the shaft 105 is rotatable relative to handle 104 by manipulation of rotation collar 135 that is rotatably coupled to projecting portion 136 of the handle. The moveable handle portion 128a is further configured with a ratchet-detent member 137a that engages detents 137b in handle portion 128b which is adapted to releasably maintain the handle portions and working end 110 in a selected articulated shape. By moving the moveable handle portion 128a toward an 'open' position A, the working end 110 will return to a linear configuration as shown in FIG. 1. Actuator buttons 138a and 138b are provided in the grip portion 128a for changing the RF power level, but also can be configured for ON-OFF actuation of they system and RF power.

Figure 4:
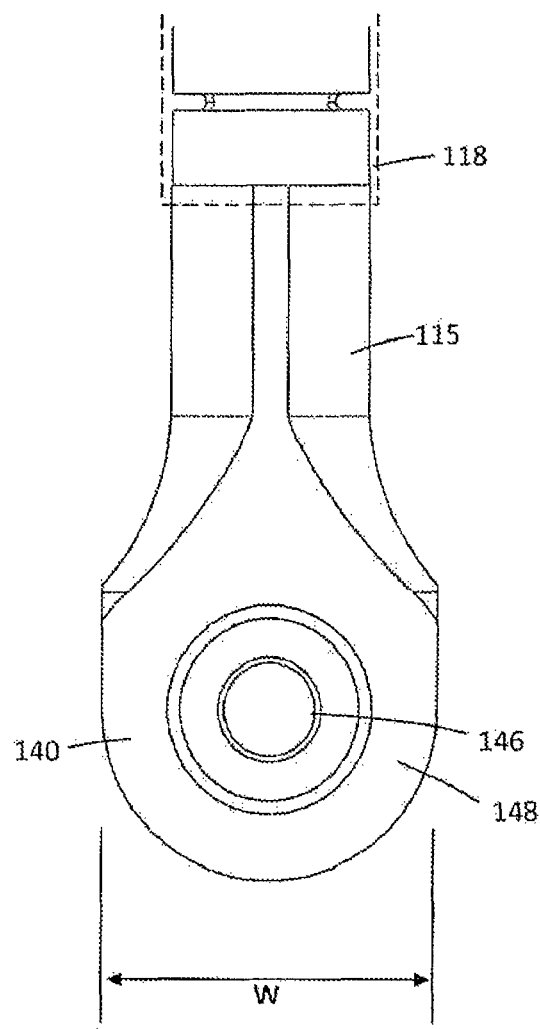
FIG. 4 is a plan view of the distal ablation body portion of the device of FIG. 1.

Now turning to FIGS. 3-6, the plasma generating system within the working end 110 is shown. FIGS. 3-4 depict one example of distal plasma ablation body portion 115 in a perspective view and in a plan view. In FIGS. 3 and 4, it can be seen that the distal body portion 115 has an expanded width relative to shaft 105 and in one embodiment can extend to a width W ranging from about 4.0 mm to 8.0 mm. FIG. 3 illustrates that the thickness T of the distal body portion is similar to the diameter of shaft 105, for example about 3.0 mm.

Figure 5:
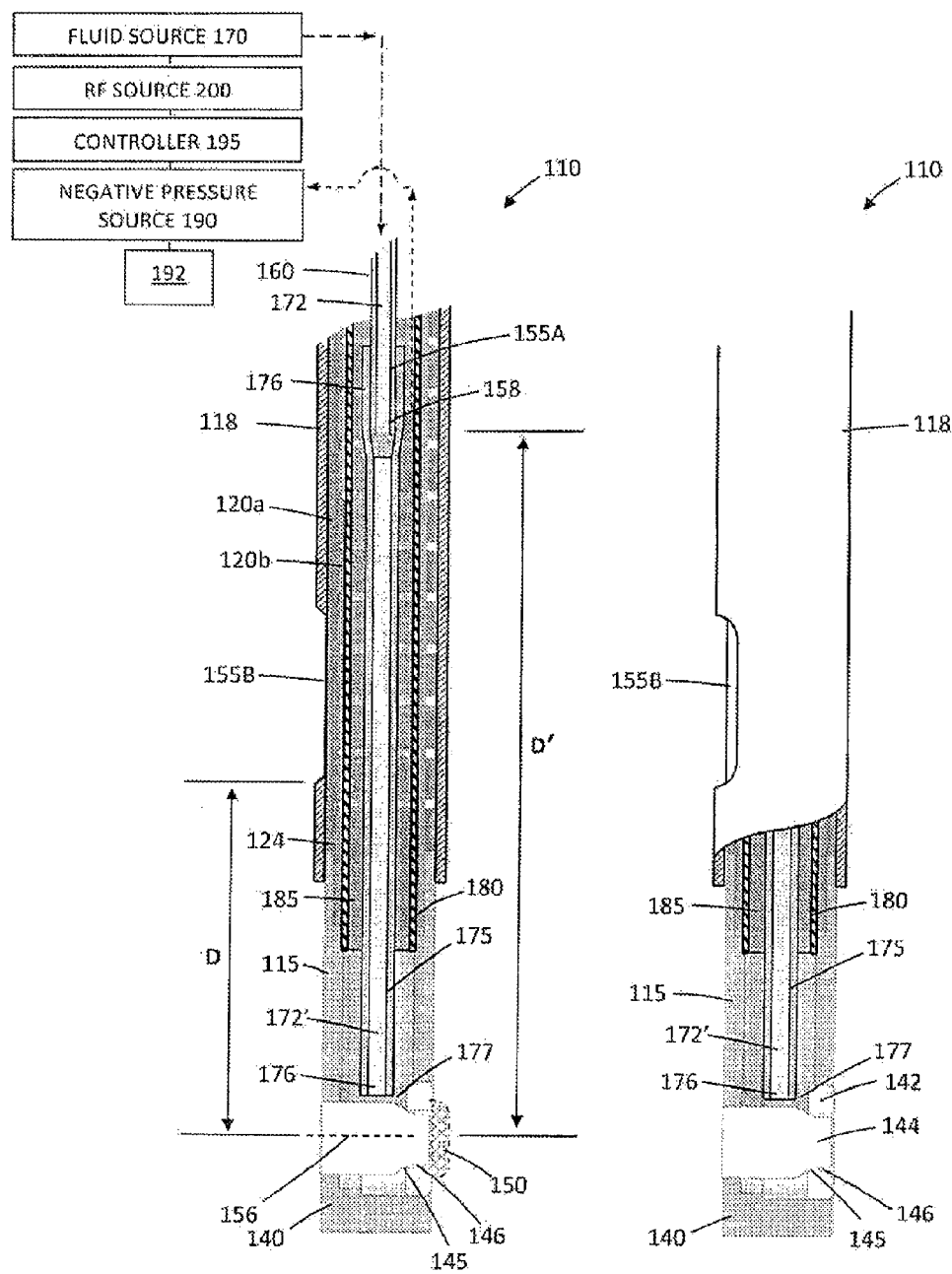
FIG. 5A is a sectional longitudinal view of the working end of the device of FIG. 1 showing the slotted sleeves configured for articulation.
FIG. 5B is a cut-away view of the working end similar to FIG. 5A showing an electrode arrangement.
Figure 6:
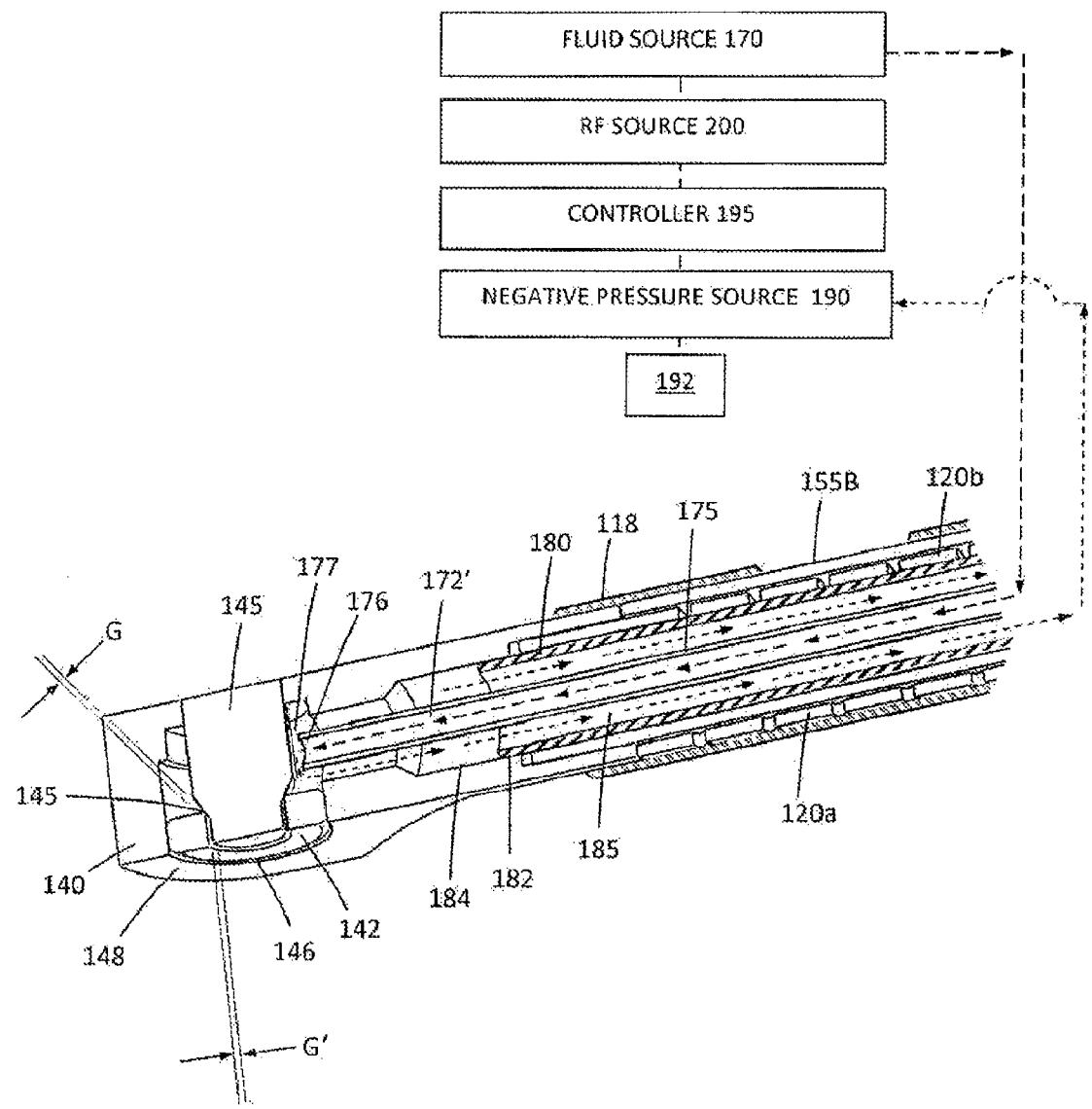
FIG. 6 is a cut-away view of the distal ablation body portion of the device of FIG. 1 further showing fluid flow pathways.

Of particular interest, referring to FIGS. 3-6, the entirety of the distal body portion 115 consists of electrically non-conductive materials which can comprise ceramics or a combination of ceramic and polymeric materials. In one embodiment shown in FIGS. 5A, 5B and 6, the body portion 115 comprises a PEEK housing 140, annular or donut-shaped ceramic element 142 that surrounds a core ceramic member indicated at 144. The ceramic annular element 142 and the ceramic core 144 are press-fit and bonded to bores in housing 140 to provide a very slight annular gap 145 having dimension G between the ceramic element 142 and ceramic core 144. Of particular interest, the fluid flow restriction caused by the gap 145, as will be described below, is designed to focus electrical energy density to generate plasma in gap 145. In one embodiment, the dimension G of gap 145 is 0.02 mm, and can range from about 0.005 mm to 0.06 mm. In FIG. 6, it can be seen the annular gap 145 transitions to slightly larger annular channel 146 having width dimension G' of about 0.08 mm to 0.10 mm which opens to the substantially planar surface 148 of body portion 115.

As will be described in detail below, the plasma ablation region 150 is adjacent and radially inward of the annular channel 146 in the planar surface 148. The finely controlled plasma can be generated to have different geometries dependent upon the operating parameters of power, fluid inflows and fluid outflows.

As described above, since the entire distal body portion 115 comprises electrically non-conductive materials, the working end 110 in FIGS. 5A-6 has its opposing polarity conductive electrodes 155A and 155B positioned remote from a plasma ablation region 150 that extends outward from gap 145 and annular channel 146 of distal body portion 115. As depicted in FIGS. 3 and 5A, the plasma ablation region 150 is indicated as a 'hatched' circular region in the center of the substantially planar surface 148 of the distal body portion 115.

Referring now to FIGS. 5A-5B, the first polarity electrode 155A comprises the distal portion of an interior tubular sleeve 160 of the shaft assembly. The second polarity electrode indicated at 155B comprises an exposed portion of outer slotted sleeve 120a wherein a portion of the flexible outer sleeve 118 is removed. The exposed portion of sleeve 120a that comprises the electrode can have an area ranging from about 1 mm$^2$ to 20 mm$^2$ and can have any shape, such as an axial, circumferential, helical or another shape.

In one embodiment depicted schematically in FIGS. 5A-5B, the first polarity electrode 155A is spaced proximally a distance D from the center or centerline 156 of the plasma ablation region 150 by at least 20 mm, 30 mm, 40 mm or 50 mm. Similarly, the distal edge 158 of second polarity electrode 155B can be spaced proximally a distance D' from the centerline 156 of plasma ablation region 152 by at least 10 mm, 20 mm, 30 mm, 40 mm or 50 mm (FIG. 5A).

Referring to FIGS. 5A-5B and 6, the electrical components and the means of operation of system can be understood. In FIG. 5A, it can be seen that a pressurized fluid source 170 is in fluid communication with lumen 172 in conductive central tubular sleeve 160 which transitions into a non-conductive sleeve 175, which can be a polymeric material or a ceramic. In one embodiment, the non-conductive sleeve 175 is a flexible, non-kinkable PEEK that can flex and bend as the working end is articulated. The distal end 158 of conductive sleeve 160 is coupled to the proximal end 176 of non-conductive sleeve 175 by any suitable means such as adhesives (FIG. 6). It be seen in FIGS. 5A-5B and FIG. 6 that lumen 172' in sleeve 175 has an open termination 176 in chamber 177 in the housing 140.

FIGS. 5A and 6 illustrate another electrically insulative component of the working end 110 that comprises flexible sleeve 180 that in one embodiment comprises a thin-wall FEP. As can be understood, FIGS. 5A and 6, the insulative FEP sleeve is adapted to provide an insulative fluid-tight layer between the first polarity electrode 150A and the slotted tubes 120a and 120b that are in the current carrying path to the exposed second polarity electrode 155B. In FIG. 6, it can be seen that the distal end 182 of the insulative sleeve 180 is bonded to sealably bonded the interior bore 184 in the housing 140.

In another aspect of the invention, still referring to FIGS. 5A-6, a circulating flow path is provided through the interior of the device (see arrows in FIG. 6) wherein positive pressure fluid source 170 supplies a saline solution that flows though lumens 172 and 172' to flow into chamber 177 of the housing 140. Thereafter, the fluid inflow reversed course and flows in the proximal direction in annular passageway 185 within the distal body portion 115 is coupled to negative pressure source 190 and a collection reservoir 192. A controller 195 is provided to control the positive and negative pressures applied within the system to provide a selected rate of liquid flow from the fluid source 170 through the device. The system further includes RF source 200 coupled by electrical leads to the first and second polarity electrodes 155A and 155B.

Figure 7:
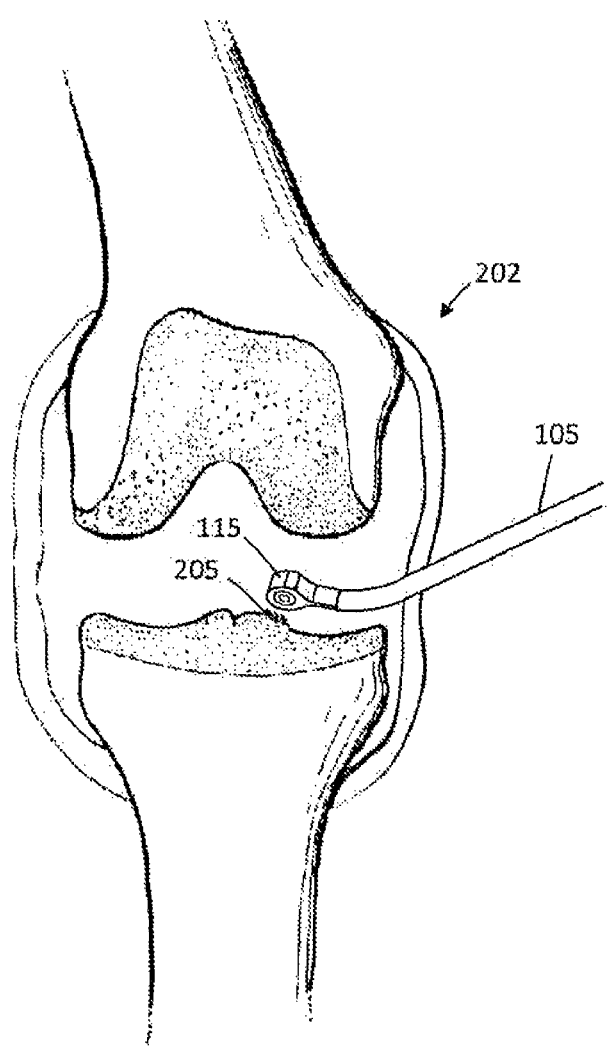
FIG. 7 is a schematic illustration of the device of FIG. 1 introduced into a knee joint to treat abnormal cartilage.

FIG. 7 is a schematic illustration of a method of use of the plasma ablation device of FIGS. 1-6 in treating cartilage, which is shown in a knee joint 202. Its should be appreciated that the device can be used to treat cartilage in any joint, such as knees, hips, shoulders, ankles and elbows.

Figure 8A:
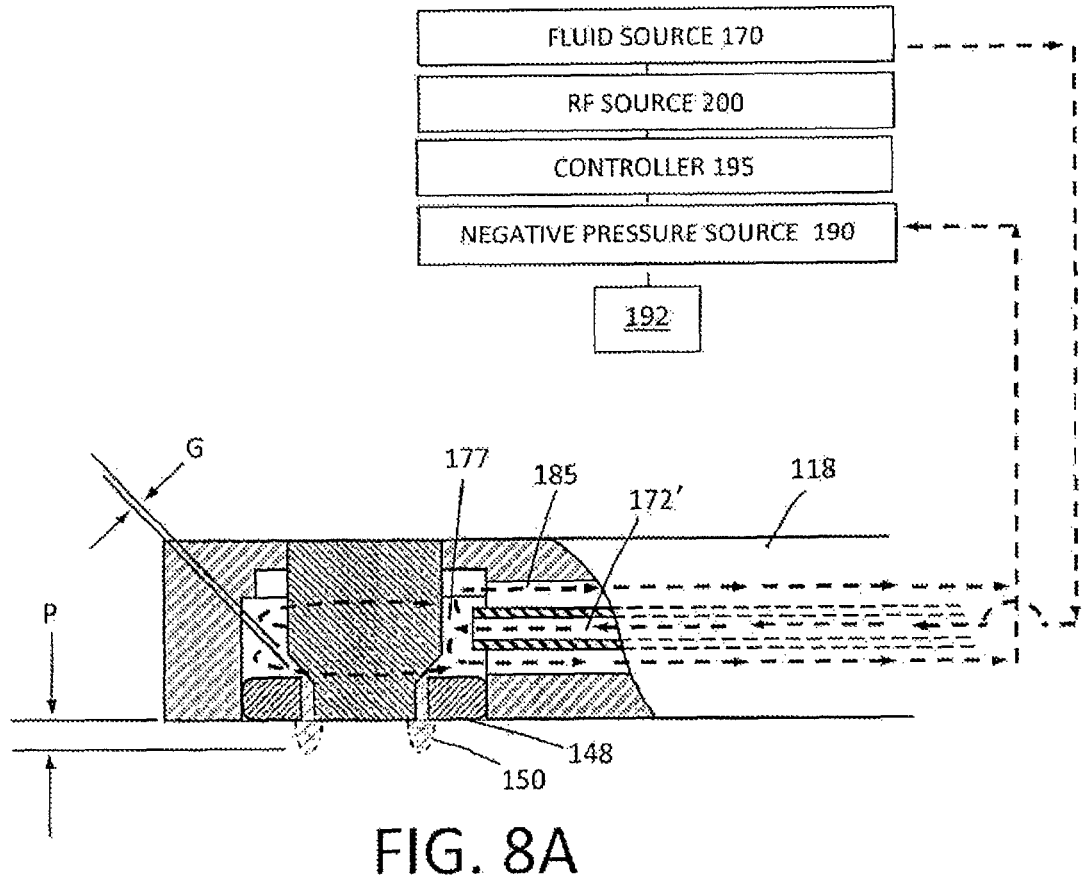
FIG. 8A is a longitudinal sectional view of the ablation body portion of the device of FIG. 1 showing fluid flows, plasma formation and the use of a low pressure chamber to provide a selected dimension of plasma propagating from a working surface.
Figure 8B:
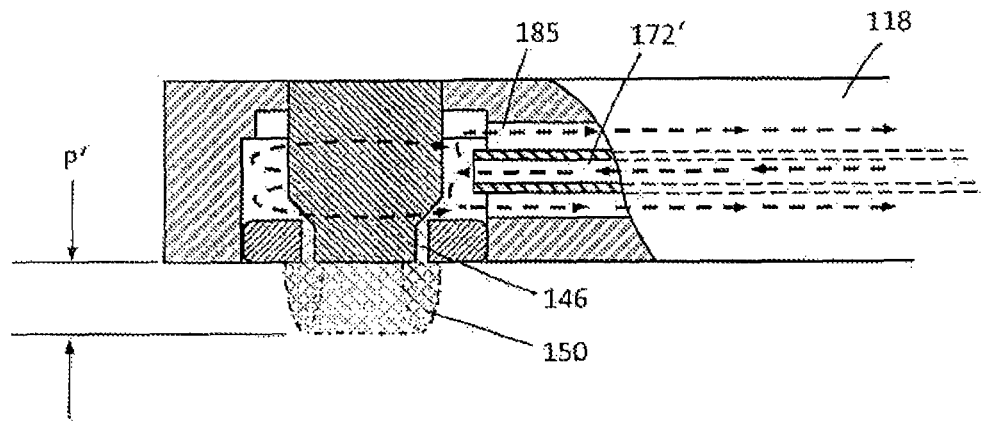
FIG. 8B is another longitudinal sectional view of the ablation body portion as in FIG. 8A with the fluid flow parameters altered to provide an alternative dimension of plasma propagating from the working surface.

FIGS. 8A-8B are cut-away schematic views of the ablation body portion 115 of working end 110 and further illustrate the dimensions of 'projection' of the plasma ablation region 150 relative to planar surface 148 of distal body portion 115 when operated under different parameters. In one embodiment shown in FIG. 8A, an inflow of fluid through lumen 172' from source 170 is provided at a flow rate 10 ml/minute. The outflow of fluid through annular lumen 185 provided by negative pressure source 195 is provided at a flow rate greater than the inflow rate, and in this example is greater than 13 ml/minute. Thus, if the working end is immersed in fluid, such as in an arthroscopic procedure, and the pressurized fluid source 170 and the negative pressure source 195 are actuated without activating the RF source 200, the device will suction fluid from the arthroscopic working space into the interior chamber 177 of the device through annular gap 146—and then outwardly through lumen 185 into the collection reservoir 192. In other words, the inflows and outflows will not be in equilibrium when the RF is not actuated, resulting in suctioning of fluid from the working space. Thus, one aspect of the invention is to provide a system controller 195 that operates the inflow and outflow subsystems to thereby create a substantially low pressure in chamber 177 before the actuation of RF wherein the low pressure allows for generation of a plasma ablation region 150 with unique characteristics.

FIG. 8A depicts the ablation body portion 115 operating under first operating parameters which results in plasma ablation region 150 extending a distance P from the planar surface 148. In FIG. 8A, the operating parameters include creating very low pressures in chamber 177, for example with outflow pressure exceeding inflow pressure by greater than 10%. In operation, when the plasma is generated or ignited by actuation of RF source 200, an equilibrium is created between the inflowing media through lumen 172, the outflowing media through lumen 185, and the plasma projection through annular gap 146. Such an equilibrium is created after the plasma is generated, which initially greatly increases pressure in chamber 177. Thus, the objective of the negative pressure source 195 is demonstrated in FIG. 8A, as the applied suction from negative pressure source 195 causes the plasma to form in a low (below ambient) pressure chamber with suction forces applied to ionized gas (plasma) and flow media that is in a liquid or vapor state. Thus, it can be understood that such negative pressures applied to chamber 177 functions (i) to control the dimension P of the plasma projected from surface 148 and (ii) to cool the plasma projected from surface 148. FIG. 8B illustrates the plasma region 150 being projected from surface 148 a certain dimension P' which is provided by reducing the net negative pressure applied to interior chamber 177 by inflow and outflow subsystems. In FIG. 8B, the operating parameters include creating a low pressure in chamber 177 wherein outflow pressure exceeds inflow pressure up to 50%.

In general, the method of the invention includes generating an equilibrium plasma in flow media within an interior of a medical device and controlling plasma projection outward of a working end surface a selected dimension ranging from 0.1 mm to 10 mm, or 0.5 mm to 5 mm.

In general, the invention is based on an appreciation of the fact that an RF-generated plasma can be controllably contained in an interior chamber 177 by providing less than ambient pressures in the interior chamber wherein the treatment plasma can be controllable emitted from at least one aperture that is in communication with the interior chamber.

Another aspect of the invention relating to tissue treatment is based on the observation that a plasma can be generated by RF energy in an interior chamber which interfaces with a negative pressure source that has the effect of cooling the plasma. In one embodiment, the temperature (i.e., average mass temperature) of the plasma is less than 80° C., less than 70° C., less than 60° C., or less than 50° C.

Another aspect of the invention is based on an appreciation of the fact that the above-described device can ablate, smooth and volumetrically remove tissue from cartilage surface without causing any thermal damage to non-targeted tissue. The energetic plasma can be generated by RF energy in an interior chamber and then projected from the device surface to ablate tissue, and the lack of collateral damage results in part from the fact that the plasma is cooled by the low pressure chamber, with the plasma temperature being selected to be less than 80° C., less than 70° C., less than 60° C. or less than 50° C.

Figure 9A:
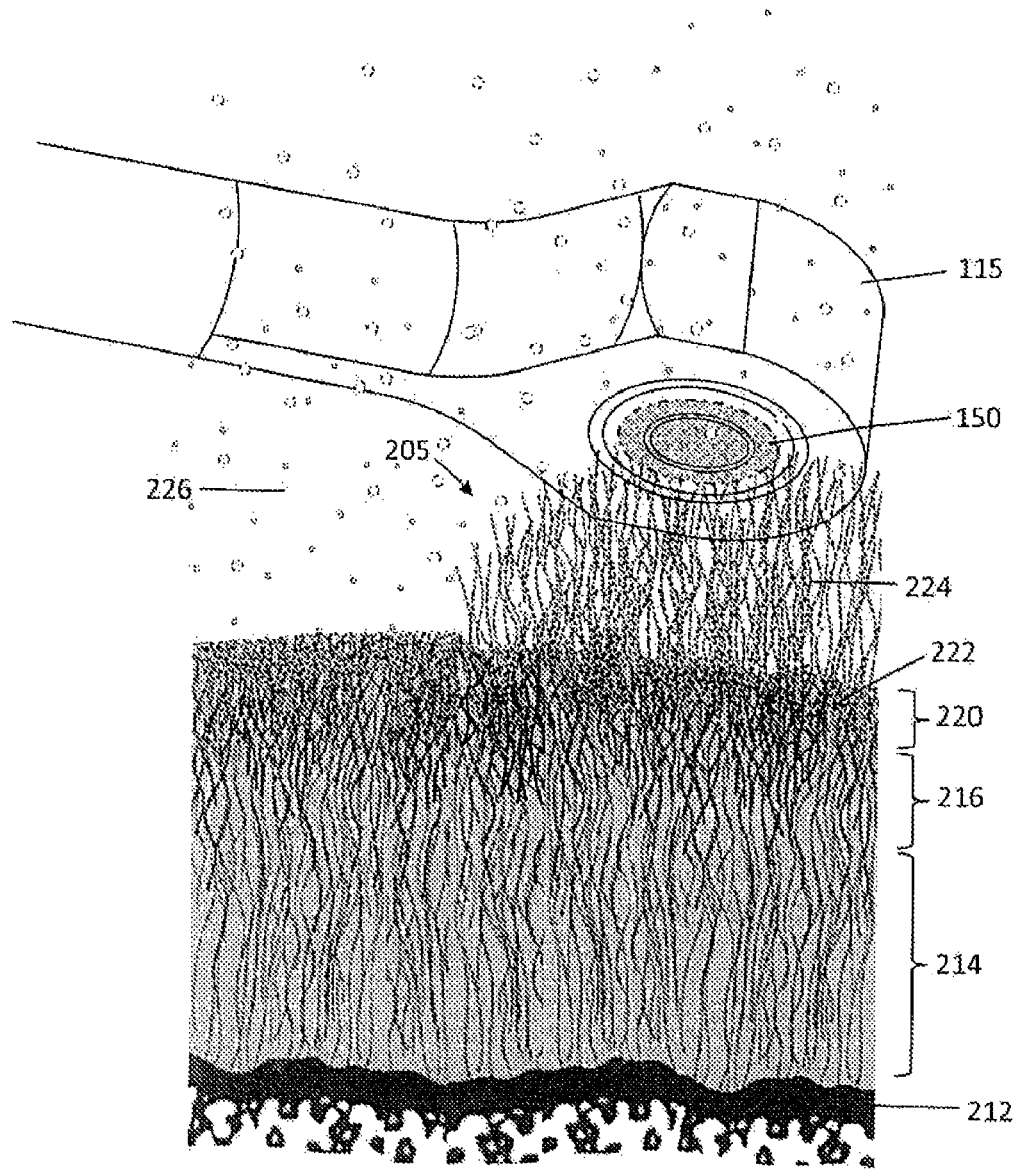
FIG. 9A is an illustration of a method of the invention in ablating fibrillation in cartilage tissue.
Figure 9B:
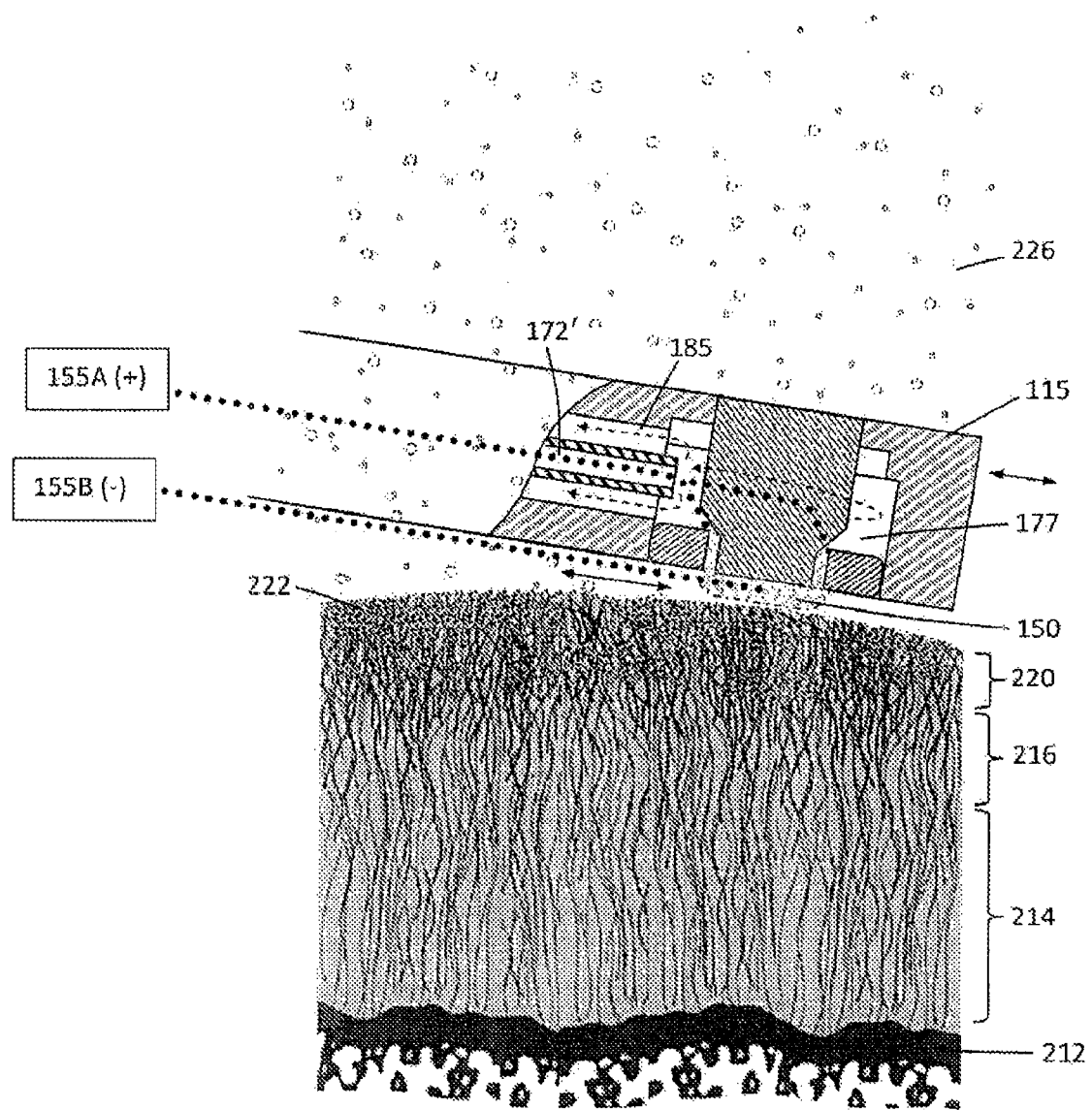
FIG. 9B is another illustration of the method of FIG. 8A which results in a smooth cartilage surface without thermal damage to the cartilage tissue.

FIGS. 9A-9B illustrate a method of the invention in treating damaged region 205 of articular cartilage, such as in a patient's knee as shown in FIG. 7. In FIG. 9A, a sectional view of a small a portion of a patients joint shows the cortical or subcondral bone 212, and cartilage layer which consists of radial zone 214, transitional zone 216, and tangential zone 220. The zones 214, 216 and 220 each are characterized by differing collagen fiber orientations with the surface zone having collagen fibers and fibril oriented mostly parallel to the cartilage surface. A common form of chondromalacia or damaged cartilage is shown in FIG. 9A which consists of a fibrillated cartilage surface, wherein collagen fibril bundles 222 of the tangential zone 220 are disrupted and fibril ends 224 float outward from the cartilage surface. Such articular cartilage damage is typically only identified after an MRI scan or when the physician view the joint with an arthroscope. The grading of cartilage damage uses the following nomenclature: Grade 0, the cartilage is normal and intact; Grade 1 cartilage has some softening and blistering; Grade 2 has partial thickness (less than 50%) defects or minor tears in the cartilage surface; Grade 3 has deeper defects (more than 50%) and Grade 4 has full thickness cartilage loss with exposure of the subchondral bone 212.

The device of the present invention is adapted for smoothing a fibrillated cartilage surface as depicted in FIGS. 9A and 9B. FIG. 9A schematically illustrates the ablation body portion 115 introduced into saline 126 that fills the joint space. FIG. 9A further depicts the plasma ablation region 150, which can have a temperature of less than 50° C., extending outward from the device to ablate and remove the fibril ends 224 that are floating into the joint space. FIG. 9B illustrates that cartilage surface after ablation and removal of the fibril ends 224 resulting in a smooth cartilage surface. Tests have been performed with the device of FIGS. 5A-9B on human cartilage tissue immediately after such tissue was removed from a patient in a 'total knee' replacement operation. It was found that the treated cartilage surface was very smooth when compared to prior art bi-polar electrode devices with exposed electrodes. In another important aspect of the invention, tests have shown that the plasma region 150 as depicted in FIGS. 9A-9B produce no thermal effects or cell death in the cartilage surface. Tests were performed using confocal laser microscopy as described in Edwards, R, "Thermal Chondroplasty of Chondromalacic Human Cartilage An Ex Vivo Comparison of Bipolar and Monopolar Radiofrequency Devices," *The American Journal of Sports Medicine* (2002) Vol. 30, No. 1, p 90. In tests of the present invention, no significant chondrocyte death was found as determined by cell viability staining in conjunction with confocal laser microscopy methods. In contrast, in the Edwards article above, all prior art RF devices that were tested caused substantial cell death in cartilage tissue.

Figure 10A:
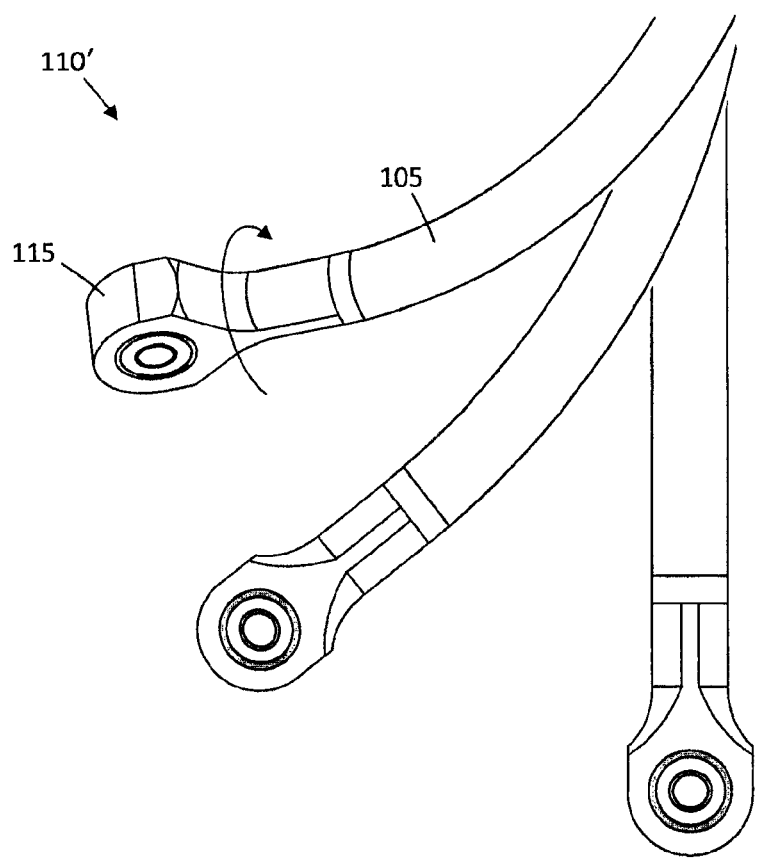
FIG. 10A is an illustration of an alternative embodiment of a working end that is articulatable with an independently rotatable ablation body portion.
Figure 10B:
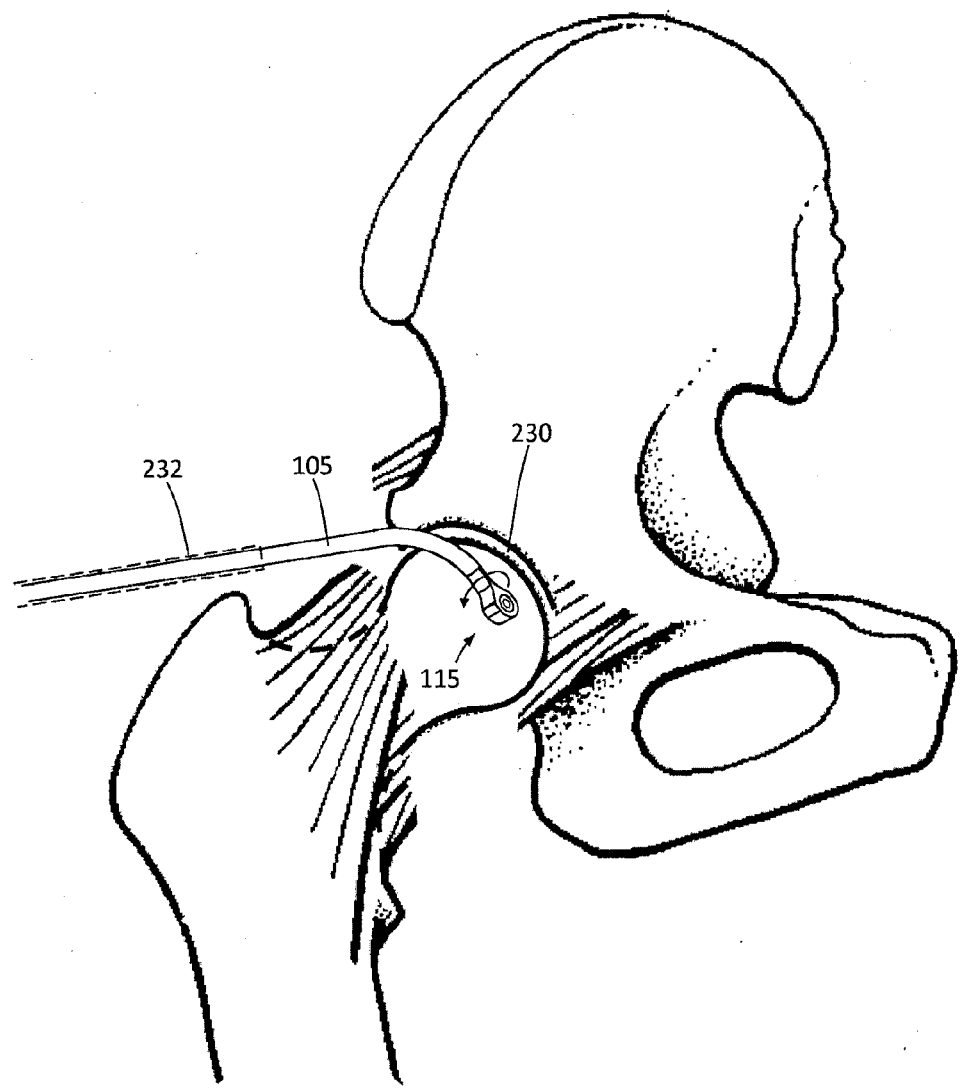
FIG. 10B is a schematic view of the working end embodiment of FIG. 10A being positioned in a hip joint to treat abnormal cartilage.
Figure 11:
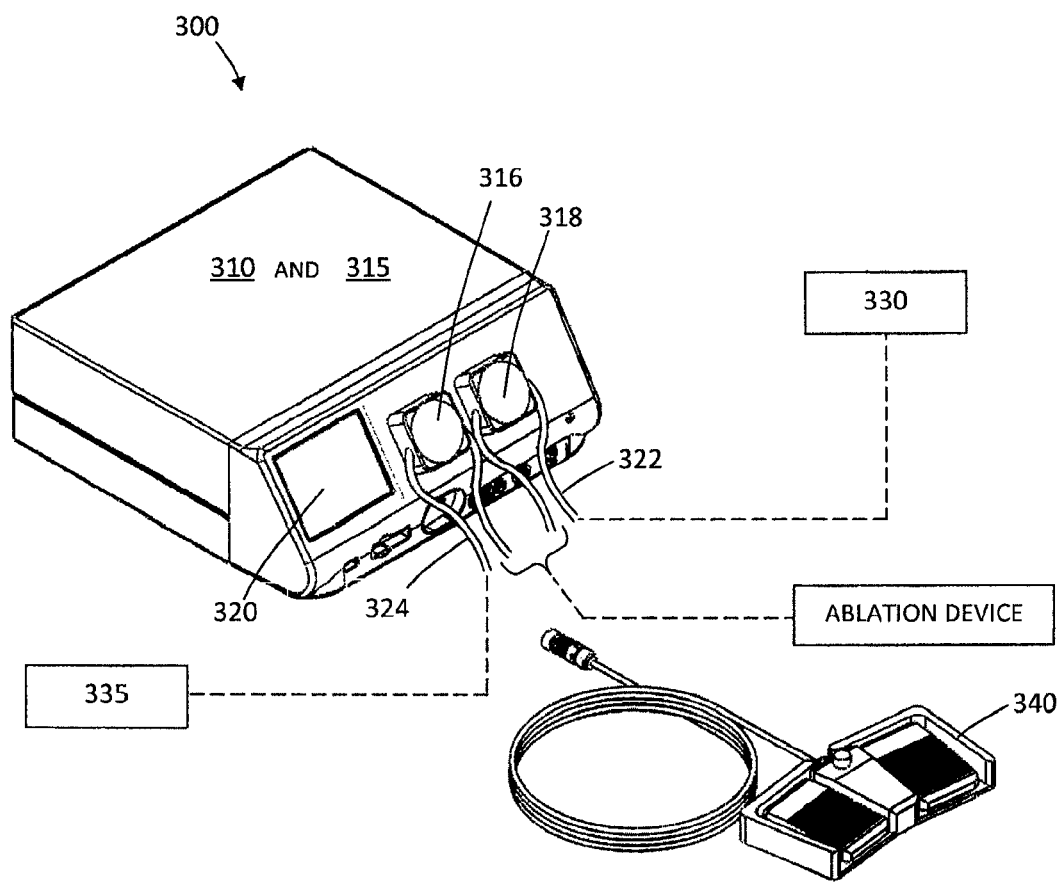
FIG. 11 is a schematic view of a RF generator, controller housing and peristaltic pumps corresponding to certain embodiments of the invention.

FIG. 10A illustrates another embodiment of working end 110' wherein the ablation body portion 115 is rotatable relative to shaft 105 no matter how the shaft is articulated. This is accomplished by providing an additional rotatable, torqueable sleeve 230 that carries the ablation body portion 115 and is rotatable within outer articulating sleeve assembly 232. FIG. 11 is a schematic illustration of the working end of FIG. 10A being used in a hip joint 240, wherein the device is introduced through an access cannula 245. After being deployed in the joint space with the introducer shaft 105 being articulated, the ablation end 115 can be rotated (see arrow) to orient the plasma to treat targeted cartilage tissue.

FIG. 11 illustrates a controller box or housing 300 that combines an RF generator source 310, computer controller 315 and positive and negative pressure subsystems configured for operating the ablation devices described above and below. The RF source 310 can be a conventional generator as is known in the art operates at within the range of 100 kHz to 550 kHz, and in one embodiment operates at 150 kHz. The front panel of controller housing 300 carries the exposed roller pump portions of first and second peristaltic pumps 316 and 318 as are known in the art that can be configured as the positive and negative pressure subsystems. The controller and ablation system can be operated from the touch screen display 320. FIG. 11 further shows single-channel or multi-channel tubes 322 and 324 that are detachably coupled to each peristaltic pump 316 and 318 to deliver positive pressure and negative pressure to the ablation device (see FIG. 1). The system further includes a fluid or saline source 330 connected to a positive pressure source to provide fluid inflows to the ablation device and a collection reservoir 335 associated with at least one negative pressure source to collect aspirated fluid and ablation by products. A footswitch 340 is provided for ON-OFF operation of the system and the RF source, although operating controls also can be provided in the handle of the device.

Figure 12A:
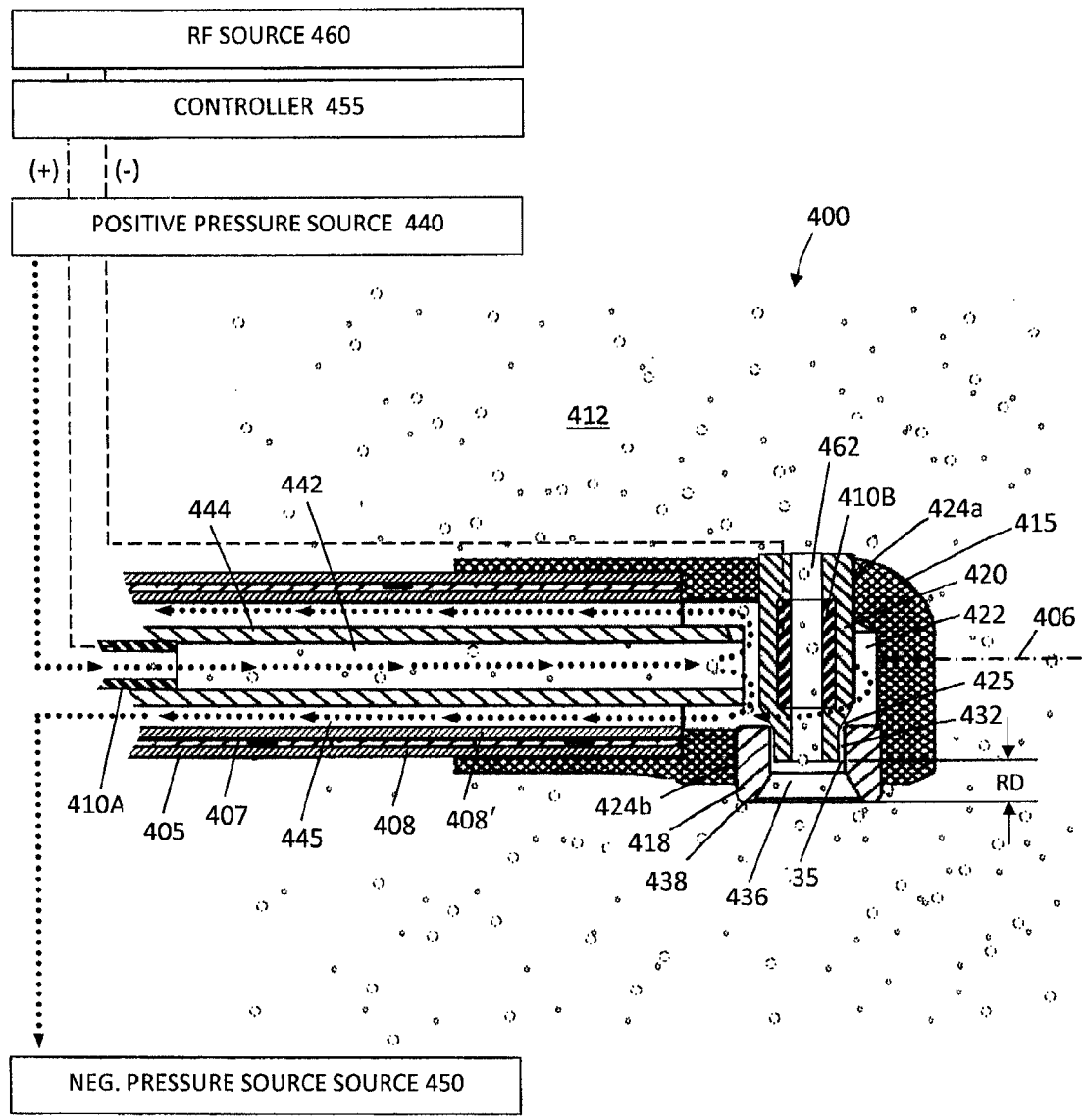
Figure 12B:
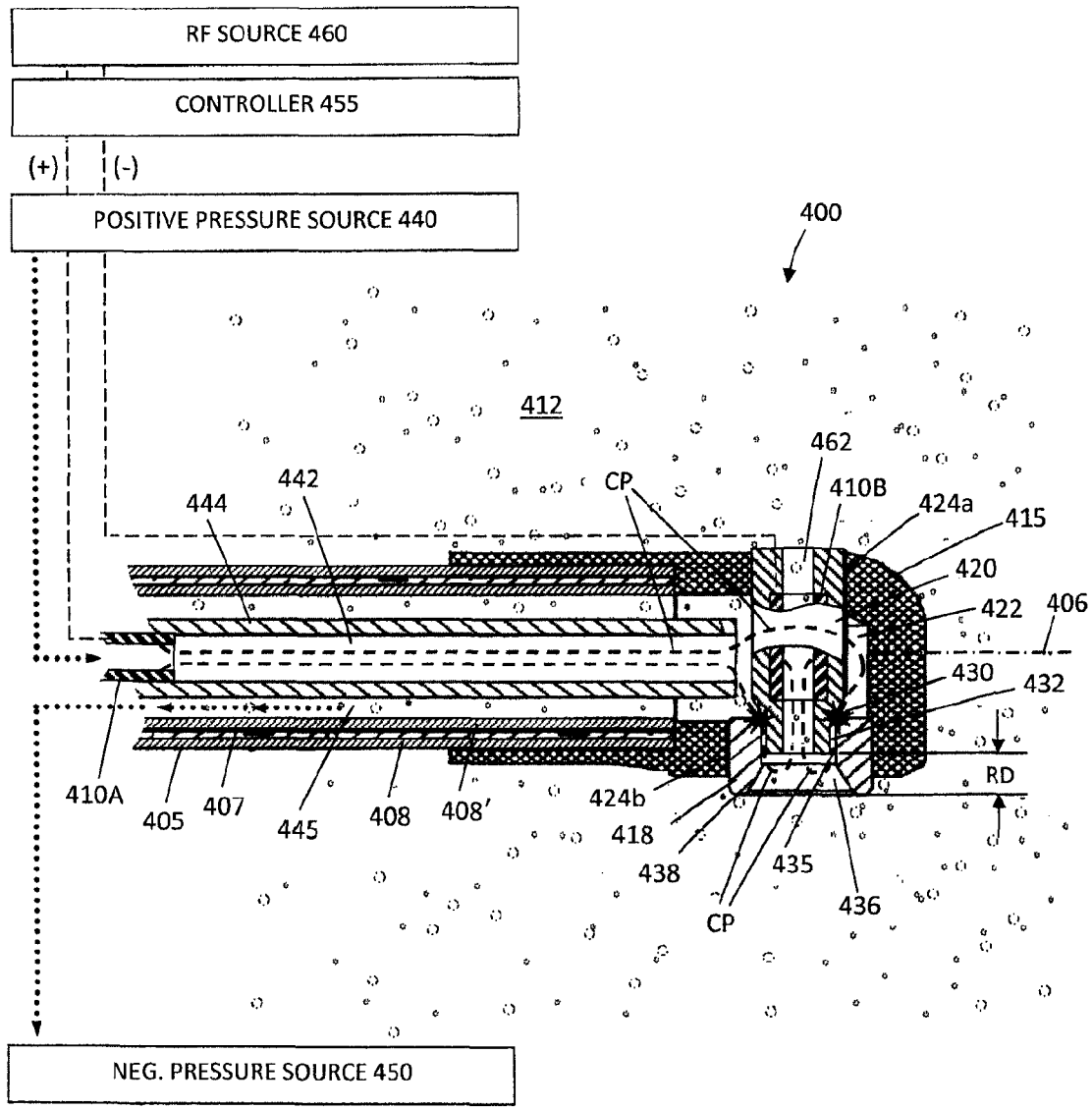
FIG. 12B is a schematic cut-away view of the working end of FIG. 12A showing the RF current paths which can be substantially confined to the interior of the working end.

FIGS. 12A-12B illustrate another variation of a plasma ablation working end 400 that configured for chondroplasty procedures. The working end 400 of FIG. 12A is carried at the distal end of shaft 405 and is based on the same operational principles described above in the embodiment of FIGS. 3-6. The shaft 405 extends about axis 406 and can comprise a thin-wall stainless steel tube 407 with insulative inner and outer coatings or layers 408 and 408'. The variation of FIGS. 12A-12B differs in that both first and second polarity electrodes, 410A and 410B, are disposed in interior passageways or regions of the device remote from articular tissue targeted for treatment. This configuration of the opposing polarity electrodes 410A and 410B provides for increased control over RF current paths in the immersed working space which consists of saline 412. More particularly, the electrode configuration can confine RF current paths substantially to the interior channels of the working end 400 and thus limit RF energy density in articular tissue to prevent active Joule heating of such tissue. In other words, the working end variation of FIGS. 12A-12B insures that targeted tissue can be treated with a low temperature plasma alone, which can best be described as "plasma etching" of such articular tissue. Such plasma etching can smooth the cartilage surface without causing thermal damage to cartilage below the articular surface.

The embodiment of FIGS. 12A-12B has a distal body portion or housing 415 that consists of electrically non-conductive materials such as a ceramic or polymer. In the embodiment shown in FIG. 12A, the housing portion 415 is a ceramic mated with an annular, donut-shaped ceramic element 418 that partly surrounds a core ceramic member 420. The annular element 418 and ceramic core 420 extend transversely through interior chamber 422 and are bonded in bores 424a and 424b in housing 415 to provide the small annular gap 425 as described previously in which plasma formation is initiated. The annular gap 425 has a dimension as described above to function as a flow restriction wherein plasma 430 (FIG. 12B) can be controllably ignited as described in the previous embodiment. In FIG. 12A, it can be seen that the annular gap 425 transitions into annular channel 432 which has an open termination indicated at 435 from which plasma is projected outwardly. In this embodiment, the open termination 435 is within a recess or concavity 436 in the surface or perimeter 438 of body portion 415. More in particular, the open termination 435 is spaced inwardly from surface 438 a recessed dimension RD that can range from 0.5 mm to 5.0 mm. In operation, the system parameters can be modulated to cause the plasma to be projected outwardly a selected dimension from the open termination 435 of annular channel 432 into the concavity 436.

Still referring to FIG. 12A, the circulating saline flow paths are provided through the interior of the device (see dotted lines and arrows in FIG. 12A) wherein positive pressure fluid source 440 supplies a saline solution that flows though lumen or first channel 442 in insulative sleeve 444 into chamber 422 of the housing 415. Thereafter, the fluid inflow reverses course in the interior chamber 422 which may also be described as a flow transition zone herein. The fluid then can flow in the proximal direction in the concentric passageway or second channel 445 that extends through the distal body portion 415 and shaft 405 and is coupled to negative pressure source 450 and collection reservoir 335 (see FIG. 11). As can be seen in FIG. 12A, the interior chamber 432 or transition zone also communicates with annular gap 425 and annular channel 432 which also is called a third channel herein. A controller 455 is provided to control the positive and negative pressures applied within the system to provide a selected rate of liquid flow from the fluid source 440 through the device. The system further includes RF source 460 that is operatively connected to the first and second polarity electrodes, 410A and 410B. As can be seen in FIGS. 12A and 12B, the second polarity electrode 410B is positioned in the interior of a passageway 462 that extends transverse to the axis of the shaft 405 with open ends on both sides of the working end. Thus, the passageway 462 has a dimension and configuration that permits saline 412 to flow into the passageway 462 as soon as the working end is immersed and thus electrode 410B will be in contact with the conductive saline 412 in the working space while the electrodes is maintained spaced apart from targeted tissue.

In another aspect of the invention, referring to FIG. 12B, it can be seen that RF current paths CP can extend from first polarity electrode 410A through interior chamber 422 and annular channel 432 to the second polarity electrode 410B in passageway 462 without extending substantially outward from the exterior surface 438 of the working end. This aspect of the invention allows for control of plasma as it projects outward from exits annular channel 432 and can confine plasma with the recess 436 in the surface which in turn can control any potential RF energy density is tissue. The plasma's geometry further can be controlled by modulating the operating parameters of applied RF power, fluid inflows and fluid outflows which control operating pressure in interior chamber 422.

Referring to FIGS. 12A-12B, the looped inflow and outflow subsystems provide operating parameters as described previously wherein very low pressures can be created in interior chamber 422 during plasma generation, for example with outflow pressures exceeding inflow pressures by greater than 10%. In one aspect of the invention, the negative pressure source 450 functions to modify the plasma (initiated in gap 425 and then extended outwardly through channel 432) from a volatile plasma to a non-volatile plasma. The term 'volatile' plasma, as used herein, is meant to describe the gaseous plasma media in its dynamic phase-transitioning stage, as saline is phase-transitioned instantly form liquid to water vapor and then to an ionized gas. In such a phase-transitioning or 'volatile' plasma, there is substantial popping, bubble formation and bubble collapse. Such a volatile plasma with bubble formation and collapse is undesirable in the volume of saline 412 that fills and comprises the working space (FIGS. 12A-12B). Thus, it can be understood the negative pressures applied to chamber 422 can function to suction the bubbles and liquid media from the volatile plasma in the interior chamber 422 to thereby create a non-volatile, non-bubbling plasma that can be extended through annular channel 232 to interface with targeted tissue. As described above, the negative pressures applied to interior chamber 422 additionally function (i) to control the dimension or geometry of the plasma projected outward from open termination 435 of the annular channel 432 and (ii) to cool the plasma projected from channel 432. In FIGS. 12-12B, the operating parameters include creating a low pressure in chamber 422 wherein outflow pressure from negative pressure source 450 exceeds inflow pressure of saline by at least 10%, 20%, 30%, 40% and 50%.

In general, a method corresponding to invention comprises creating a non-volatile plasma in an immersed conductive fluid workspace and interfacing the non-volatile plasma with targeted tissue. The method comprises ablating a targeted body structure with a non-volatile, non-bubbling plasma in a fluid environment which permits endoscopic viewing in the non-bubbling environment. More in particular, the method includes positioning a probe working end in proximity to a targeted structure of a patient's body, wherein the working end includes an interior space, and creating a volatile plasma in the interior space and extending a non-volatile plasma outwardly from the interior space to interface with the targeted structure. The method includes modifying a plasma from volatile to non-volatile. The method further includes modifying the plasma by applying negative pressure to the volatile plasma to remove bubbles and liquid from the volatile plasma. The method includes igniting the plasma in flow media flowing in a looped flow through the interior space 422 in a device working end (FIGS. 12A-12B).

Figure 13:
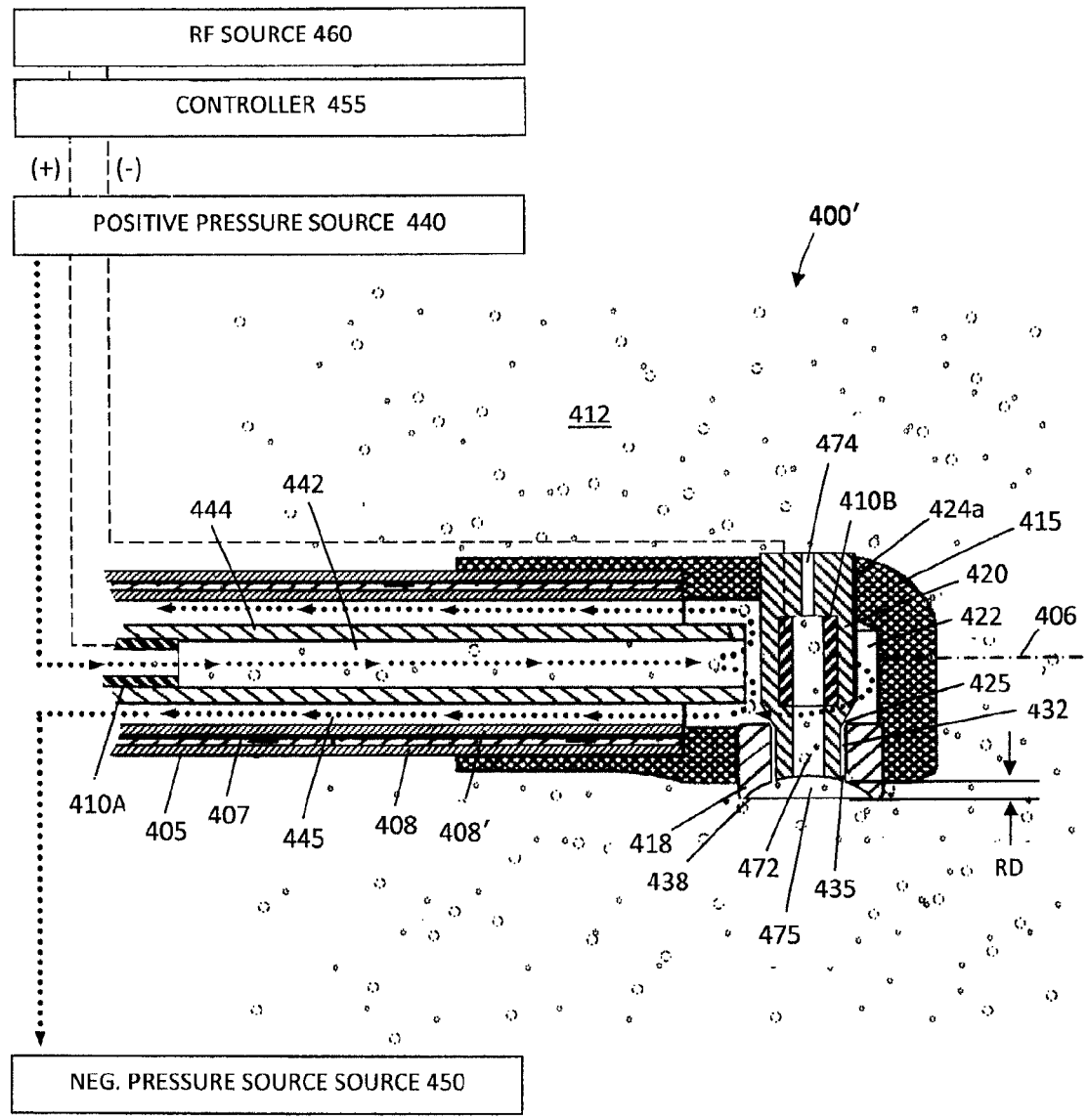
FIG. 13 is a schematic sectional view of another alternative working end with a different passageway configuration that carries an interior electrode.

FIG. 13 is a cut-away view of another embodiment of working end 400' that is similar to the embodiment depicted in FIGS. 12A-12B, in which like reference numbers indicate like features. The variation in FIG. 13 differs only in the configuration of the transverse passageway in ceramic core 420 that extends transverse to the axis 406 of shaft 405 and that carries electrode 410B. In FIG. 13, it can be seen that the transverse passageway has a non-uniform cross-section with larger diameter portion 472 transitioning to smaller diameter portion 474. This variation is adapted to substantially prevent saline flows through the transverse passageway during a treatment interval which might be induced by saline or plasma flows in annular channel 432. The variation of FIG. 13 also shows the open termination 435 of the annular channel 432 is within a smooth contour concavity 475 in the working end.

Figure 14A:
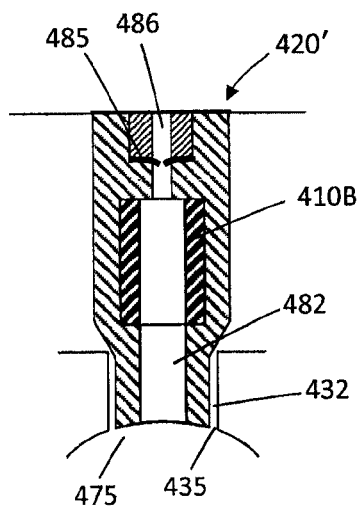
FIG. 14A is a sectional view of a ceramic core component of an alternative working end with a different passageway including a valve.
Figure 14B:
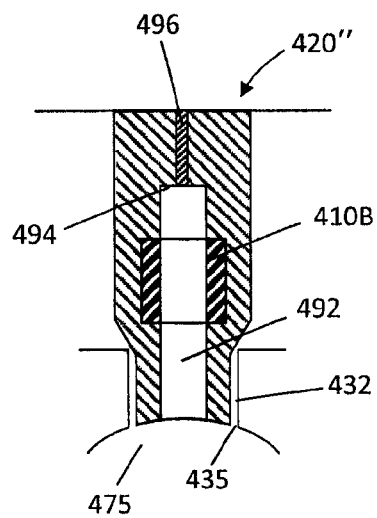
FIG. 14B is a sectional view of another ceramic core component of a working end with a different passageway including exposure to a passive conductive or capacitive material.

FIGS. 14A-14B illustrate alternative ceramic cores 420' and 420" that can be used in the working end embodiments of FIG. 12A or FIG. 13. The variations of FIGS. 14A-14B are again adapted to control saline flow in the transverse passageway in the ceramic core while still insuring that a conductive path is provided interior electrode 410B which is exposed to the passageway. In FIG. 14A, it can be seen that the transverse passageway 482 has a flap-valve 485 or any type of one-way valve in transverse passageway portion 486 to limit, but permit, saline flows into and/or through the passageway. FIG. 14B depicts a closed-end passageway 492 that carries electrode 410B. In FIG. 14B, the closed end 494 of the passageway interfaces with a conductive or capacitive material 496 that is not coupled to electrode 410B but can potentially carry current to saline in the passageway 492. It should be appreciated that the open end of the passageways 482 and 492 in FIGS. 14-14B can be oriented in either direction relative to opening 435 of annular channel 432.

Figure 15A:
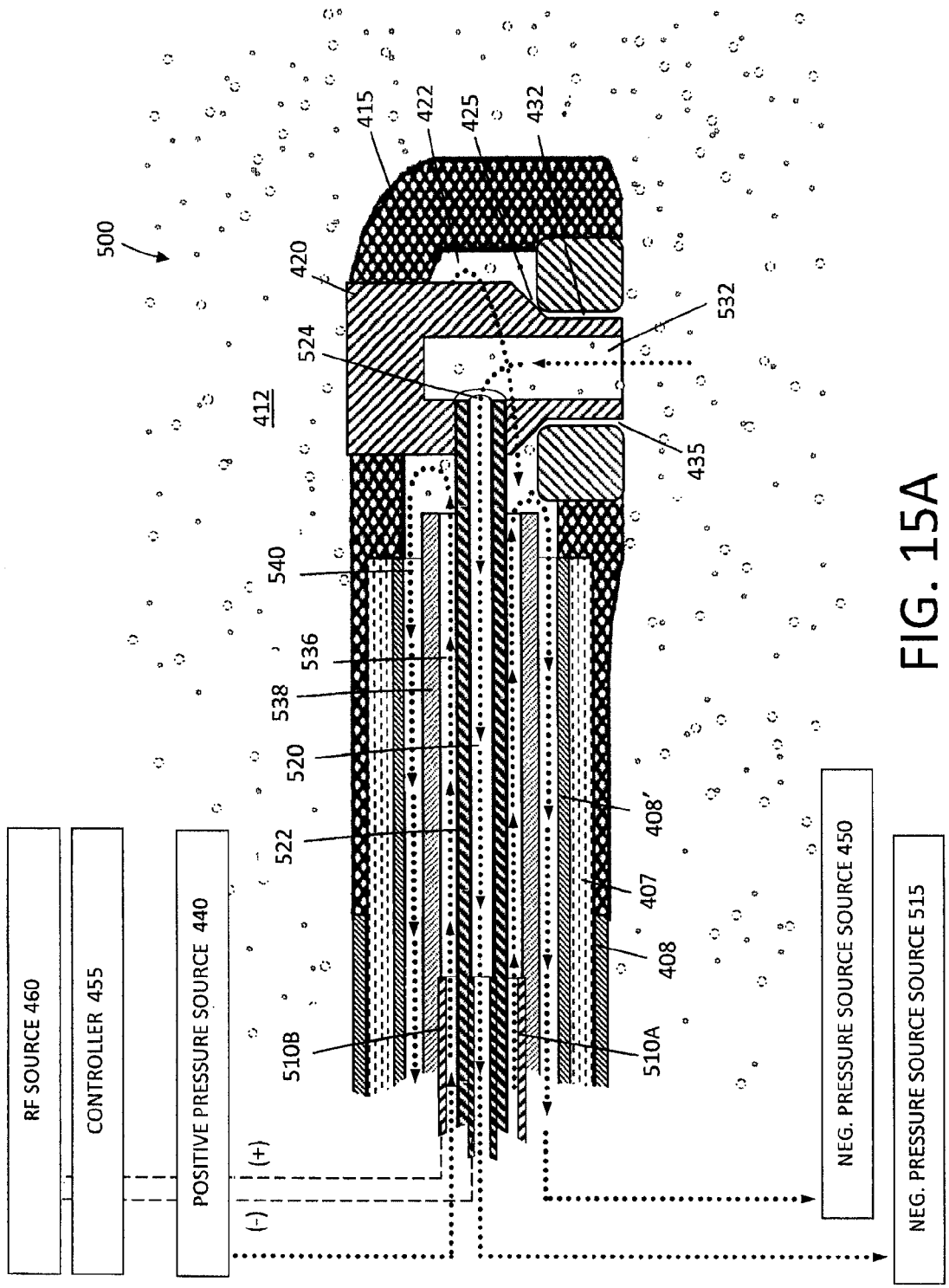
FIG. 15A is a sectional view of a working end variation configured with first and second polarity electrodes disposed in the interior of the working end, wherein one electrode is within an aspiration channel, with FIG. 15A illustrating fluid flows within the device.
Figure 15B:
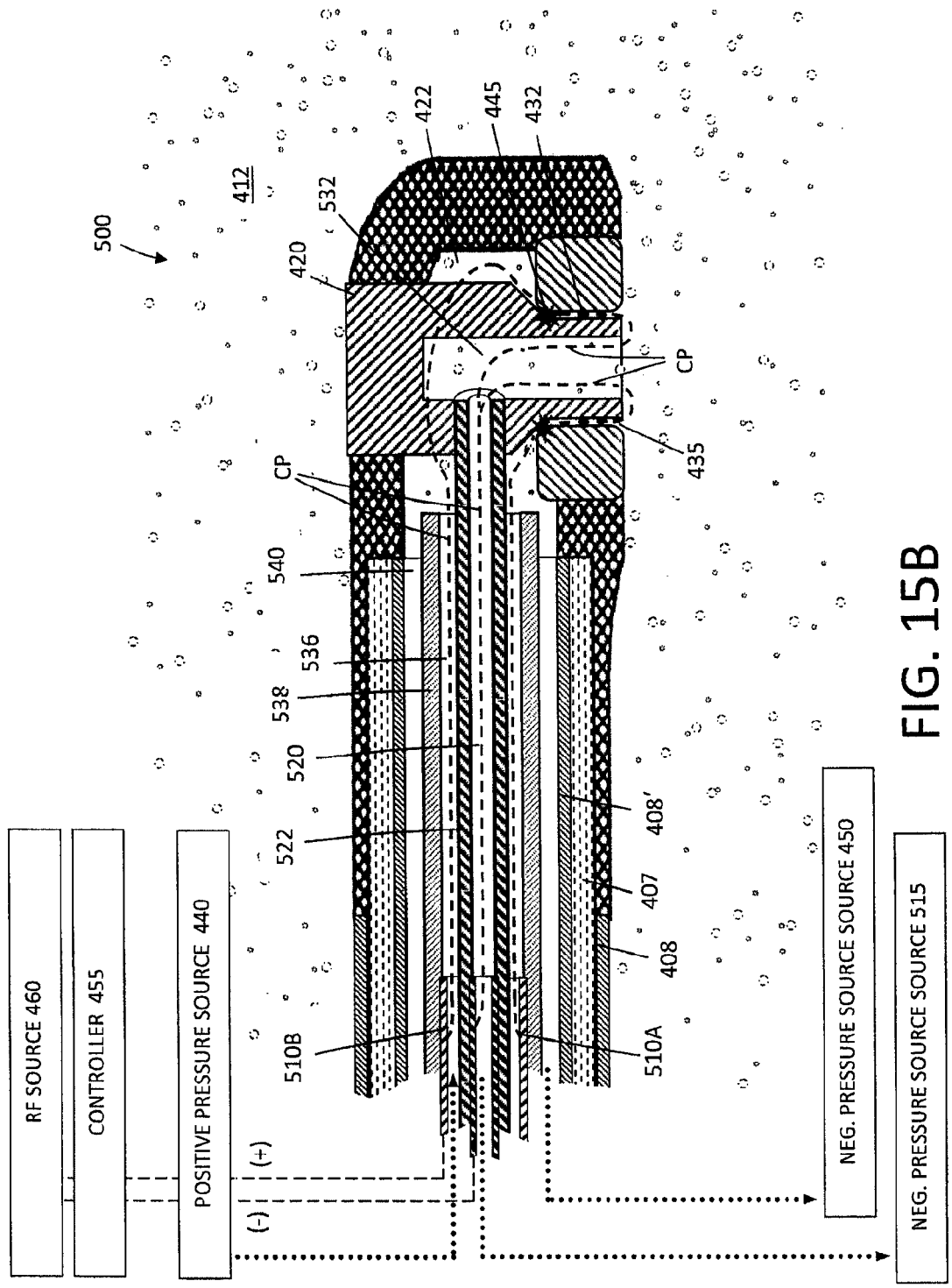
FIG. 15B is a schematic cut-away view of the working end of FIG. 15A showing the RF current paths which can be substantially confined to the interior of the working end.

FIGS. 15A-15B are cut-away views of another embodiment of working end 500 that is similar to the embodiment depicted in FIGS. 12A-12B and again in which like reference numbers indicate like features. The embodiment of variation in FIGS. 15A-15B includes opposing polarity electrodes 510A and 510B disposed within active fluid flow passageways in the interior of the working end 500. In this embodiment, a second negative pressure source 515 is provided which is configured to suction flow media and fibrillated cartilage into an interface with plasma projecting outward from the opening 435 of annular channel 432. Further, the second negative pressure source 515 can extract ablation debris and bubbles from saline 412 during operation. More in particular, the second negative pressure source 515 is coupled to aspiration lumen or fourth channel 520 in insulative sleeve 522 that extends to opening 524 in transverse passageway 532 within the ceramic cores 420. As can be seen in FIG. 15A, the saline inflow from source 440 is similar to previous embodiments wherein circulating saline inflows and outflows are provided through inflow channel 536 in insulative sleeve 538 and thereafter through interior chamber 422 and outflow channel 540. In this embodiment, the first polarity electrode 510A is carried in inflow channel 536 and the second polarity electrode 510B is carried in aspiration channel 520. FIG. 15A shows the various flow channels as being concentric for convenience, and it should be appreciated that any configuration of the multiple channels can be used.

In operation, FIG. 15A indicates the various fluid flows by dotted lines and arrows. In FIG. 15B, the RF current paths CP are shown during operation in the same manner as shown in FIG. 12B to illustrate the formation of plasma 445 in the flow restriction. As can be seen in FIG. 15B, the RF current path extends from first electrode 510A exposed to saline in flow channel 536 through the flow restriction 425 (see FIG. 15A) and then through transverse passageway 532 and lumen 520 to second electrode 510B. As in the embodiment of FIGS. 12A-12B, the RF current paths are substantially confined to the interior of the working end which lowers or eliminates RF current density in tissue. In all other respects, the working end 500 functions as described previously.

Figure 16A:
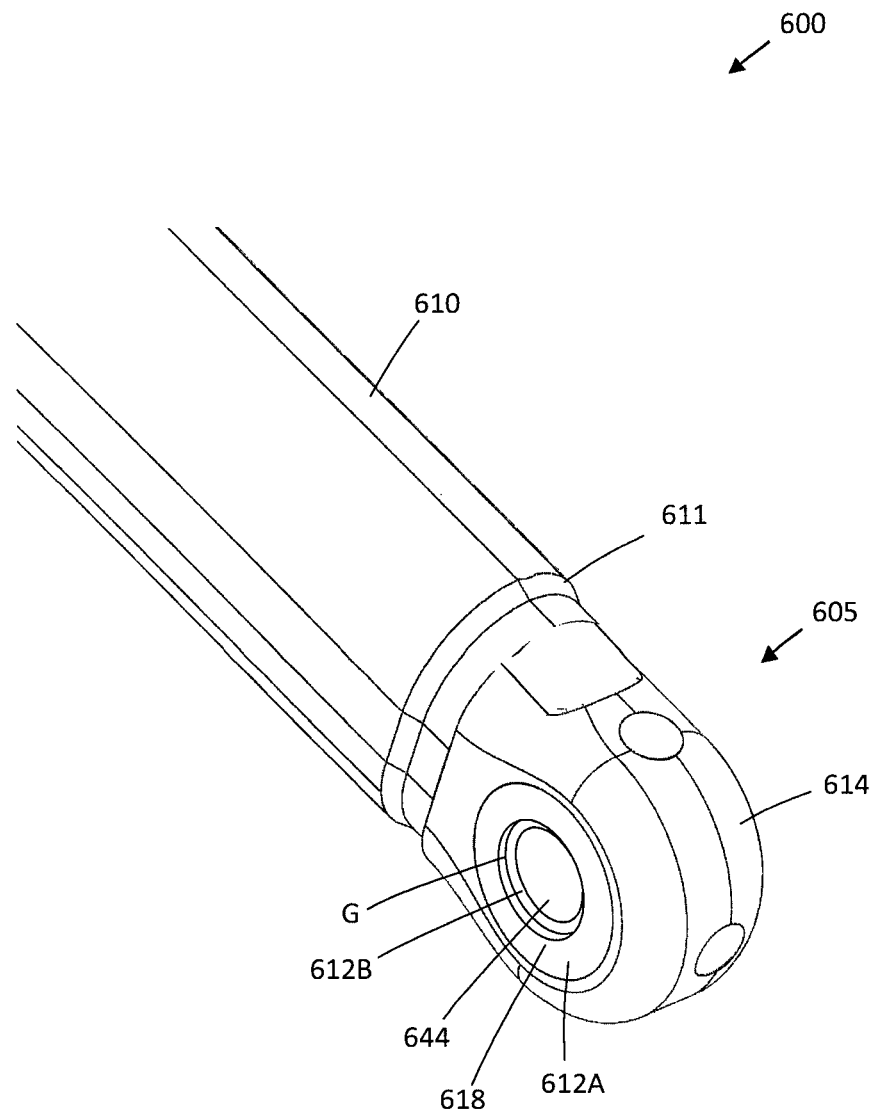
FIG. 16A is a perspective view of an alternative working end configured with first and second polarity electrodes disposed in interior channels and a tissue extraction lumen.

FIGS. 16A-18B illustrate another electrosurgical system 600 and working end 605 that is adapted for chondroplasty procedures. In FIG. 16, it can be seen that a round or oval probe shaft 610 carries a dielectric working end 605 that can comprises ceramic bodies as generally described above. The shaft 610 can comprise a stainless steel tube covered with a thin wall dielectric material 611. In one embodiment, the distal working end 605 comprises an assembly of first and second ceramic bodies 612A and 612B (e.g., zirconium) that define an interface 615 therebetween. Both ceramic bodies 612A and 612B are carried in ceramic housing 614. The interface 615 between the ceramic bodies 612A and 612B (see FIG. 18A), terminating in gap G in the surface 618, can be extremely tight and in one embodiment the interface is sufficiently fluid-tight to prevent liquid flow therethrough but still permit electrons and plasma to propagate through the interface 615. In working end 605 of FIGS. 16A-18B, the first and second polarity electrodes, 620A and 620B are disposed entirely within the interior of ceramic bodies 612A and 612B with no exposure in the working surface 618 or shaft 610.

Figure 16B:
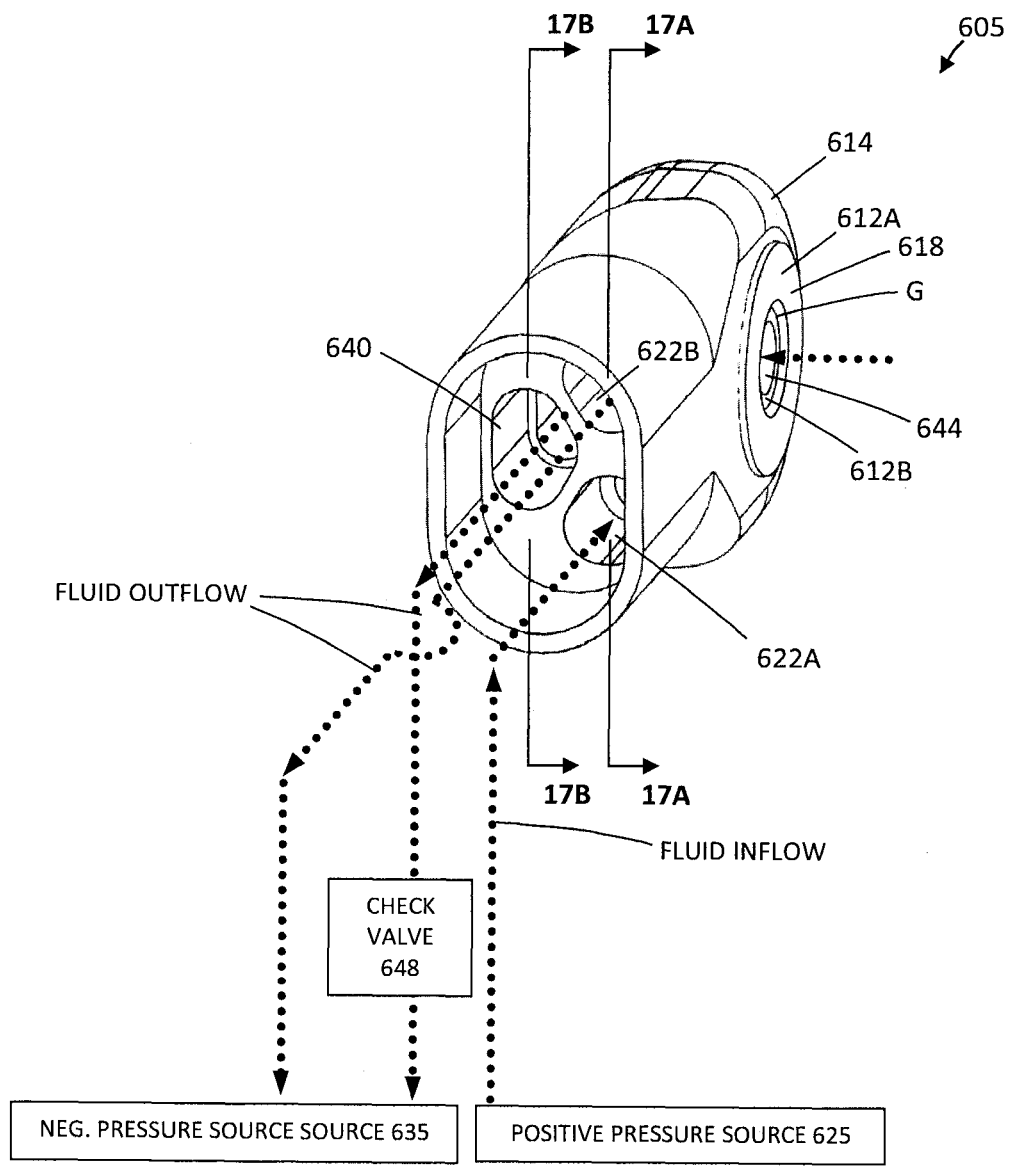
FIG. 16B is a perspective view of the working end of FIG. 16A de-mated from it shaft showing the flow channels in the working end.

Now turning to FIG. 16B, the ceramic working end 605 is shown de-mated from the shaft 610. In FIG. 16B, it can be seen that there is a looped or circulating first inflow channel 622A and second outflow channel 622B wherein a positive pressure source 625 delivers saline solution through first channel 622A and around the interior channel portion 630 (see FIG. 17A) adjacent the interface 615 between ceramic bodies 612A and 612B (see FIG. 18A). A negative pressure source 635 is configured to draw or suction the saline through channel 622B to a remote collection reservoir. In addition, the negative pressure source 635 communicates with a tissue extraction lumen 640 in the probe shaft and working end 605 which has an open termination 644 in working surface 622. In one embodiment, a single negative pressure source 635 is used to communicate with both (i) the saline outflow through second channel 622B and (ii) saline outflow through the tissue extraction channel 640. As will be described below, one embodiment provides pressure and/or a flow control mechanism positioned intermediate the negative pressure source 635 and the tissue extraction channel 640. In one such embodiment, the pressure control mechanism comprises a check valve 648 shown schematically in FIG. 16B. Such a check valve or pressure relief valve 648 can be disposed in the working end 605 or in the shaft 610 or in a handle of the device (not shown). The check valve can function to maintain negative pressure parameters in the second channel 622B and channel portion 630 (see FIGS. 17A and 18A) to maintain predetermined plasma ignition parameters in the event the tissue debris clogs the tissue extraction lumen 640.

Figure 17A:
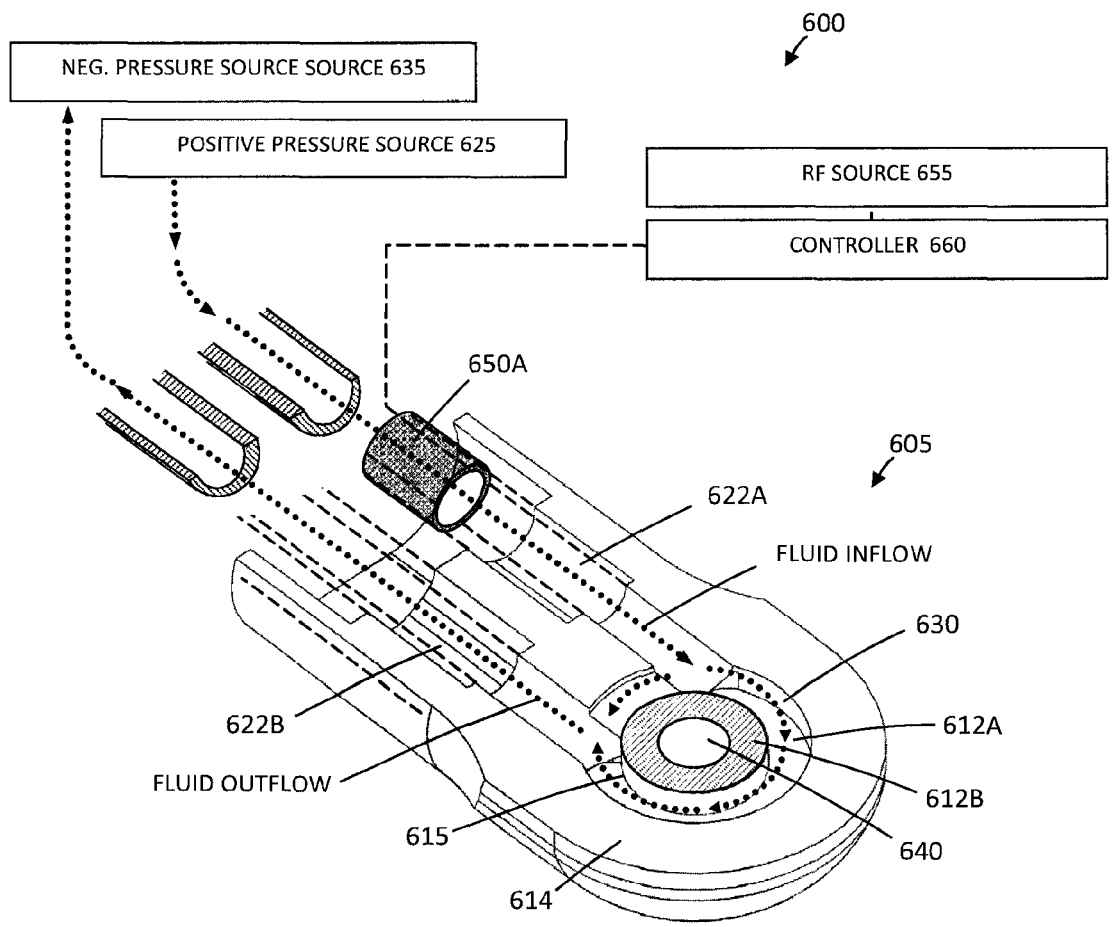
FIG. 17A is a sectional view of the working end of FIGS. 16A-16B showing a looped inflow-outflow channels and a first polarity electrode disposed in an interior channel, and illustrating fluid flows within the working end.

Now turning to FIG. 17A, a sectional view is provided through a portion of the working end 605 of FIG. 16B and more particularly through the inflow and outflow channels 622A and 622B. It can be seen how the positive pressure source 625 introduces saline through first channel 622A and then around the looped channel portion 630 adjacent the interface 615 between the ceramic bodies 612A and 612B to finally flow into the outflow channel 622*b* assisted by the negative pressure source 635. The plasma can be controlled to project through the interface 615 to the working surface 618. FIG. 17A a further shows a first polarity electrode 650A disposed in the inflow channel 622A from which RF current can flow through the interface 615 as will be described below. The electrode 650A is operatively coupled to RF source 655 and controller 660.

Figure 17B:
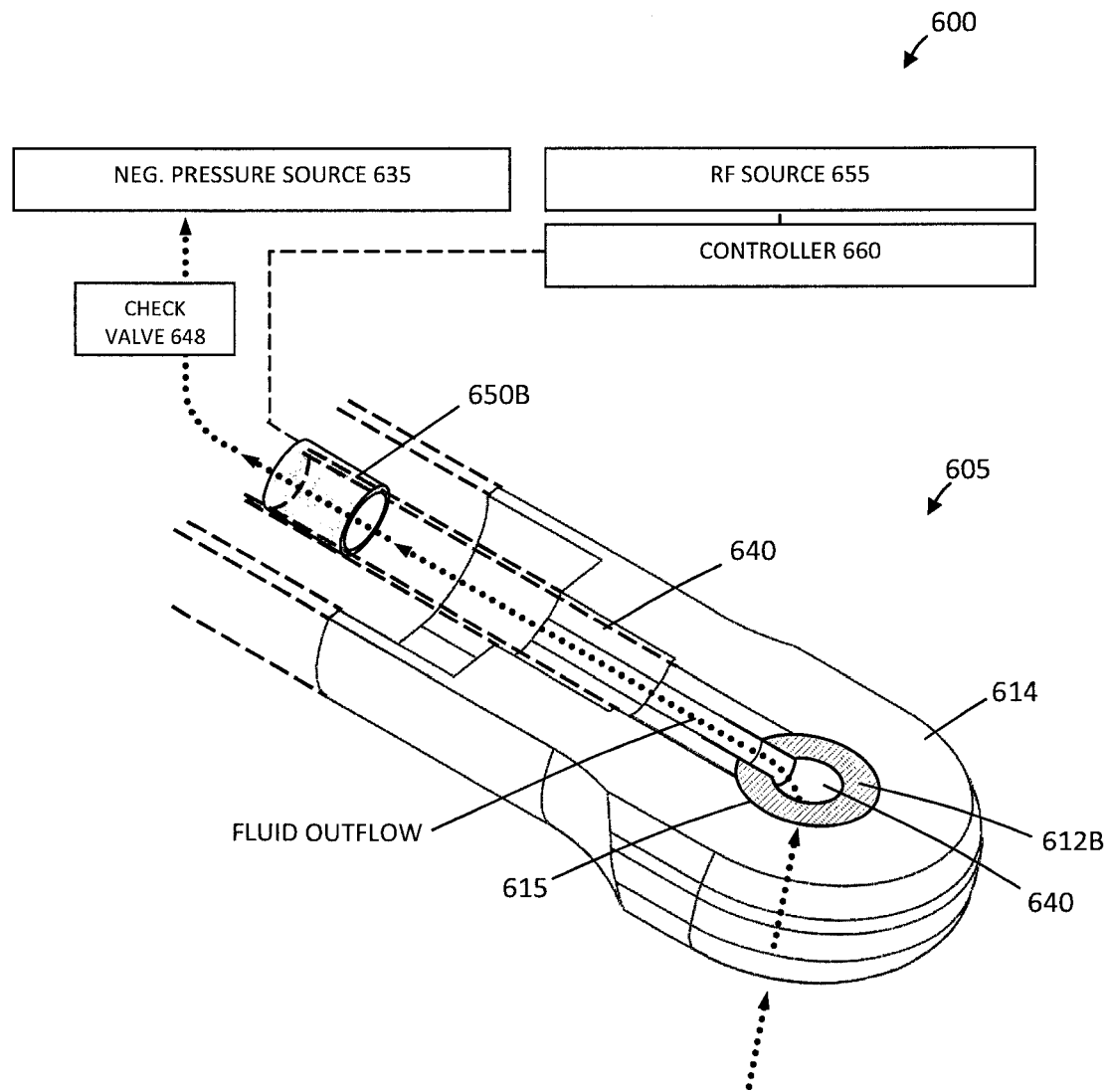
FIG. 17B is another sectional view of the working end of FIGS. 16A-16B showing a tissue extraction channel and a second polarity electrode disposed in this channel, and further illustrating a fluid flow path through the working end.

FIG. 17B is another section through working end 605 and more particularly through the tissue extraction channel 640 in the working end of FIG. 16B. It can be seen that the single negative pressure source 635 is in fluid communication with the proximal end of the tissue extraction lumen 640 as well as the second channel 622B described above. Further, a second polarity electrode 650B is disposed within the tissue extraction channel 640 so that both polarity electrodes are entirely internal to the working end 605.

Figure 18A:
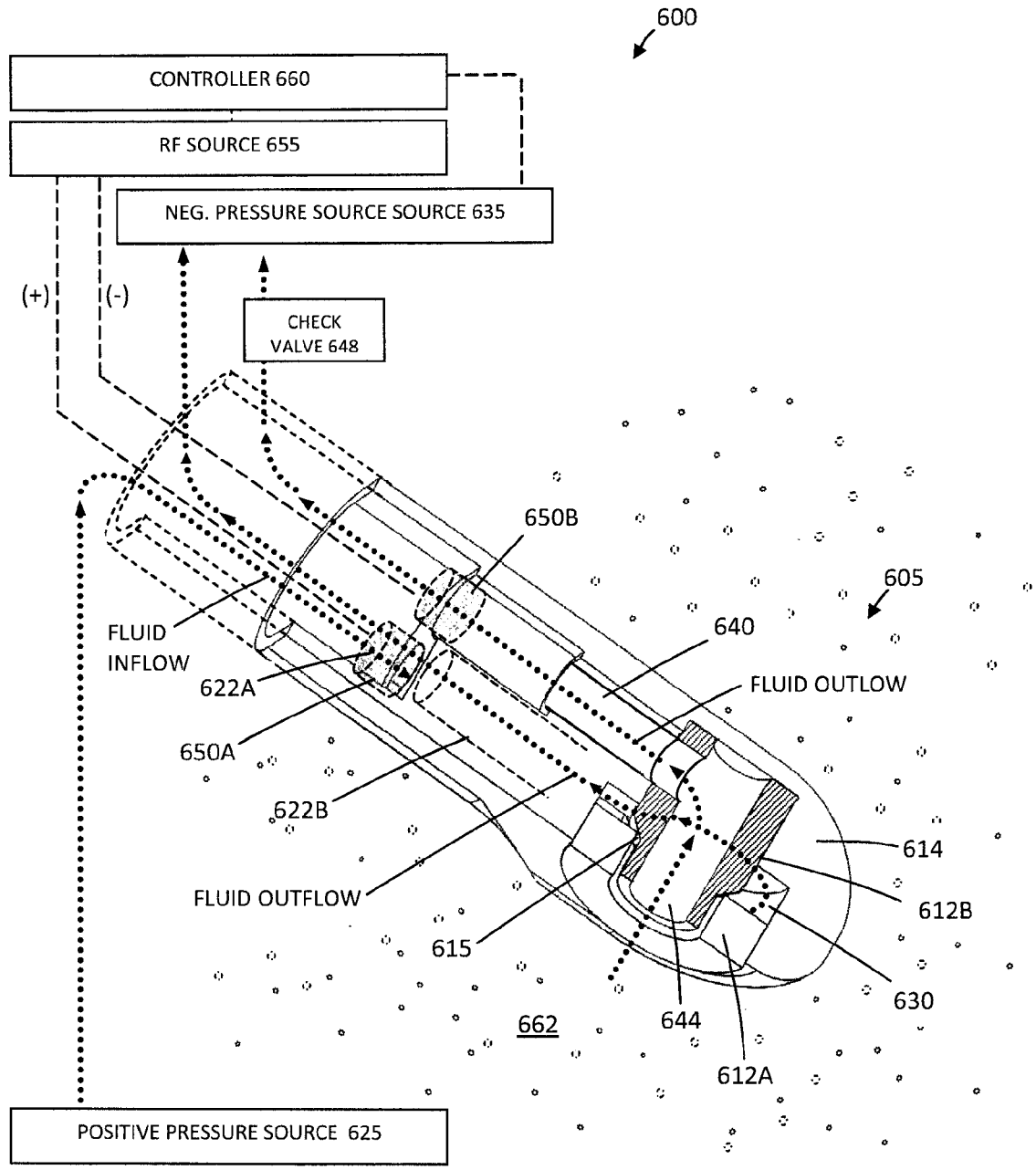
FIG. 18A is another sectional view of the working end of FIGS. 16A-16B showing fluid flows within and through the working end and first and second polarity electrodes disposed in the interior of the working end.
Figure 18B:
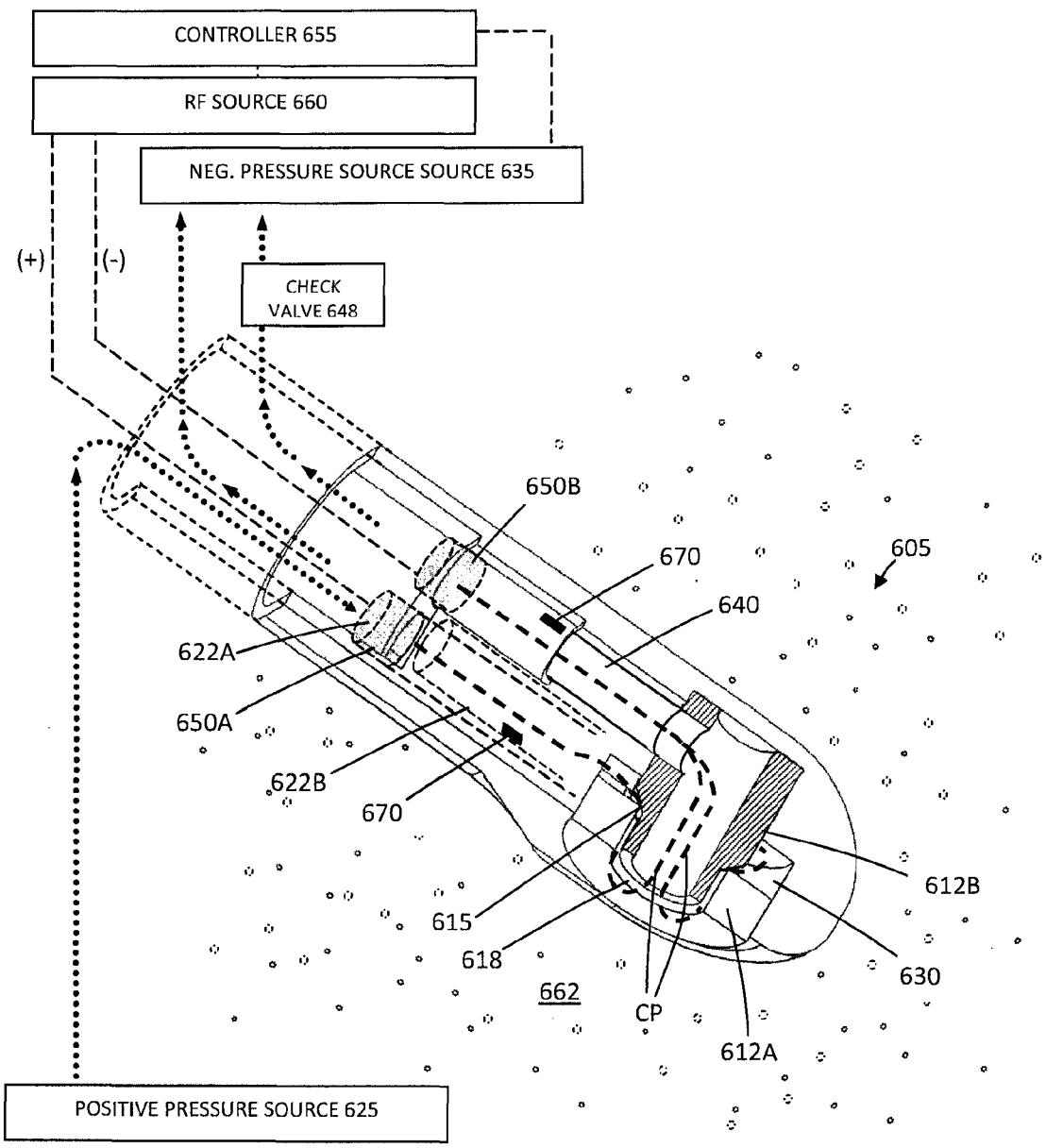
FIG. 18B is a sectional view as in FIG. 18A showing the RF current paths between the first and second polarity electrodes which are substantially confined to the interior of the working end.

FIGS. 18A-18*b* are cut-away views of working end 605 that show fluid flows and RF current paths within the working end in using the probe to treat damaged cartilage or similar tissue. Referring to FIG. 18A, the working end 605 is shown disposed in a distending fluid, such as a saline solution, in a working space 662. The dotted lines in FIG. 18A indicate potential and actual fluid flows within the working end and through the working end 604 from the working space. FIG. 18A shows that the negative pressure source 635 is coupled to both the tissue extraction lumen 640 and the outflow lumen 622B. The purpose of the pressure control mechanism or pressure relief valve 648 can be better understood from FIG. 18A. The probe and working end 605 are designed to smooth cartilage in a working space 662 and in some instances the plasma may ablate and extract fibrillations that will clog the tissue extraction lumen 640. In such an instance, there will be an imbalance in the negative pressure source 635 applying suction pressures to both channels 622B and 640. Thus, one embodiment uses as pressure relief valve 648 which can prevent excessive negative pressure from being directed to the second channel 622B when the extraction channel 640 is clogged in which case the excessive negative pressure would alter or diminish plasma formation. In another embodiment, at least one optional pressure sensor 670 (FIG. 18B) can be provided to sense pressure in either or both channels 622B and 640 wherein the sensor can be configured to signal the controller to modulate a valve (not shown) to maintain a predetermined pressure in the second channel 622B to thereby maintain plasma formation in the interface 615. In another embodiment, referring to FIG. 19, the probe can have first and second independently controlled negative pressure sources 635 and 635' coupled to respective outflow channel 622B and tissue extraction channel 640. In another embodiment, the tissue extraction channel can carry a pressure sensor 670 as described previously (see FIG. 18B) wherein the sensor can sense tissue clogging the channel in which case the controller 660 would modulate pressure in the channel between greater negatives pressures, pulsed negative pressures, positive inflow pressures, pulsed inflow pressures, or a combination of such pressure modulations designed to remove the tissue debris clogging the channel 640.

FIG. 18B illustrates the current paths CP within and about the working end 605 during operation in which plasma is generated and translated across a tissue surface. As can be seen in FIG. 18B, both the sleeve like electrodes 650A and 650B are disposed in channels 622A and 640, respectively, in the working end 605 and the RF current paths CP communicates though channel 622A, interface 615 and extraction channel 640 to provide for plasma-tissue contact while both electrodes 650A and 650B are disposed in the interior of the working end 605. Thus, the working end 605 and system creates RF current paths CP that are confined within the working end and extend only slightly into or around a portion of the working surface 618 of the probe. In one aspect of the invention, the fact that both electrodes 650A and 650B are completely internal within the working end means the no high energy densities are created about an electrode adjacent to or in contact with tissue. This in turn means that tissue cannot be heated to high temperatures or carbonized which is undesirable and can lead to elevated immune responses and delay healing of treated tissue.

Figure 19:
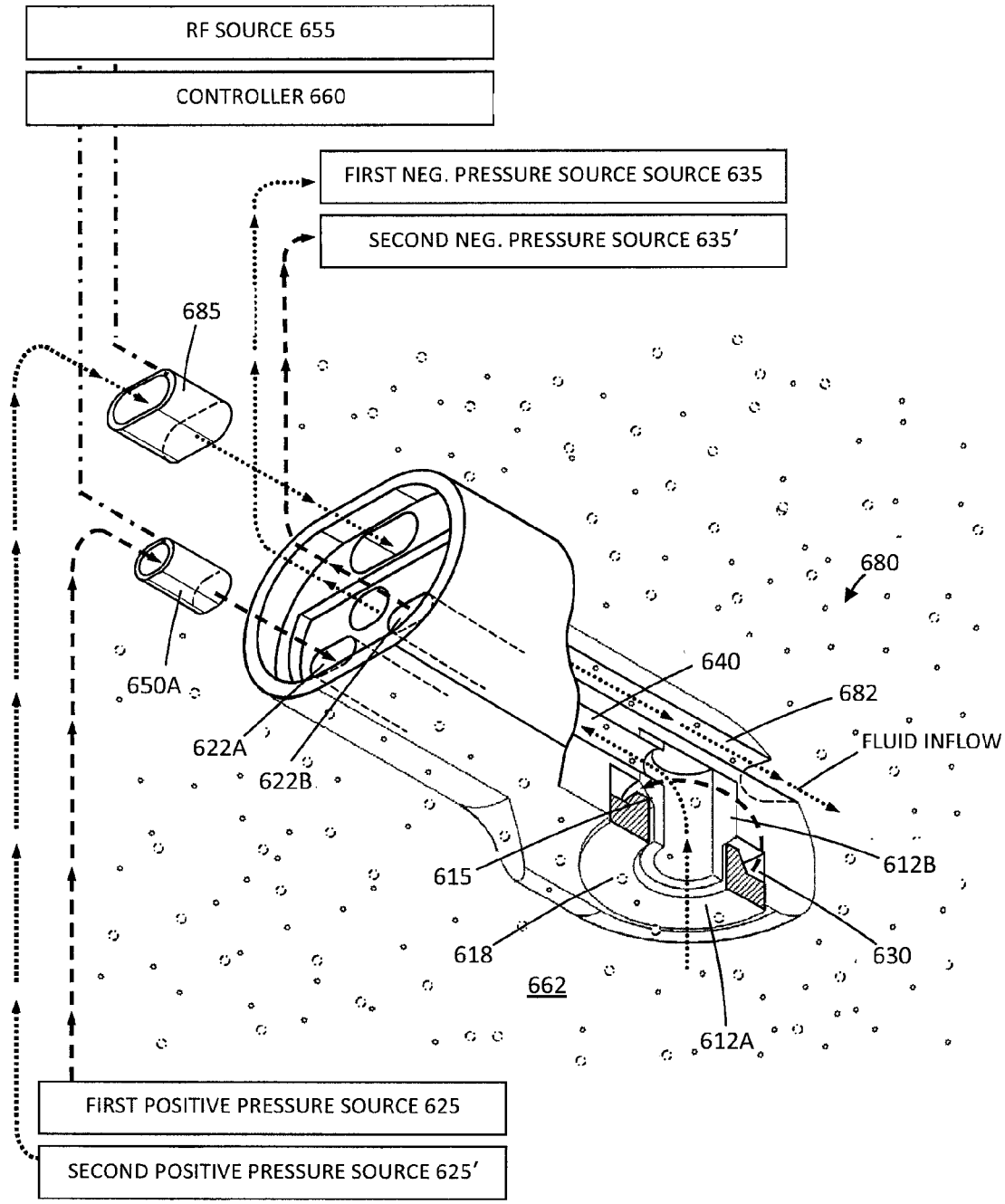
FIG. 19 is a cut-away view of an alternative working end similar to that of FIGS. 16A-18B configured with an additional inflow channel for delivering a saline distension fluid to a working space and an alternative electrode arrangement.

FIG. 19 illustrates another system and working end embodiment 680 which is similar to that of FIGS. 16A-16B except that this embodiment includes a further inflow channel 682 for delivering a saline distention fluid through probe and outwardly from the working end. In this embodiment, another internal saline flow is provided in the paths as previously described circulating through inflow channel 622A, loop channel portion 630 and outflow channel 622B. The tissue extraction channel 640 is again as described previously. The variation in FIG. 19 has first and second negative pressure sources 635 and 635' independently coupled to channel 622B and 640. The distension fluid channels 682 in FIG. 19 is operatively coupled to a second positive pressure source 625' which provides the saline distention fluid. In the working end 680 of FIG. 19, the opposing polarity electrodes 650A and 685 are disposed entirely within the interior of the device. In one embodiment, the first polarity electrode 650A again is carried in inflow channel 622A and the second polarity electrode 685 is carried in the distension fluid inflow channel 682. In operation, it can be understood that current paths CP (not shown) will extend from first polarity internal electrode 650A through interface 615 and inflow channel 682 to the second polarity internal electrode 685.

Figure 20:
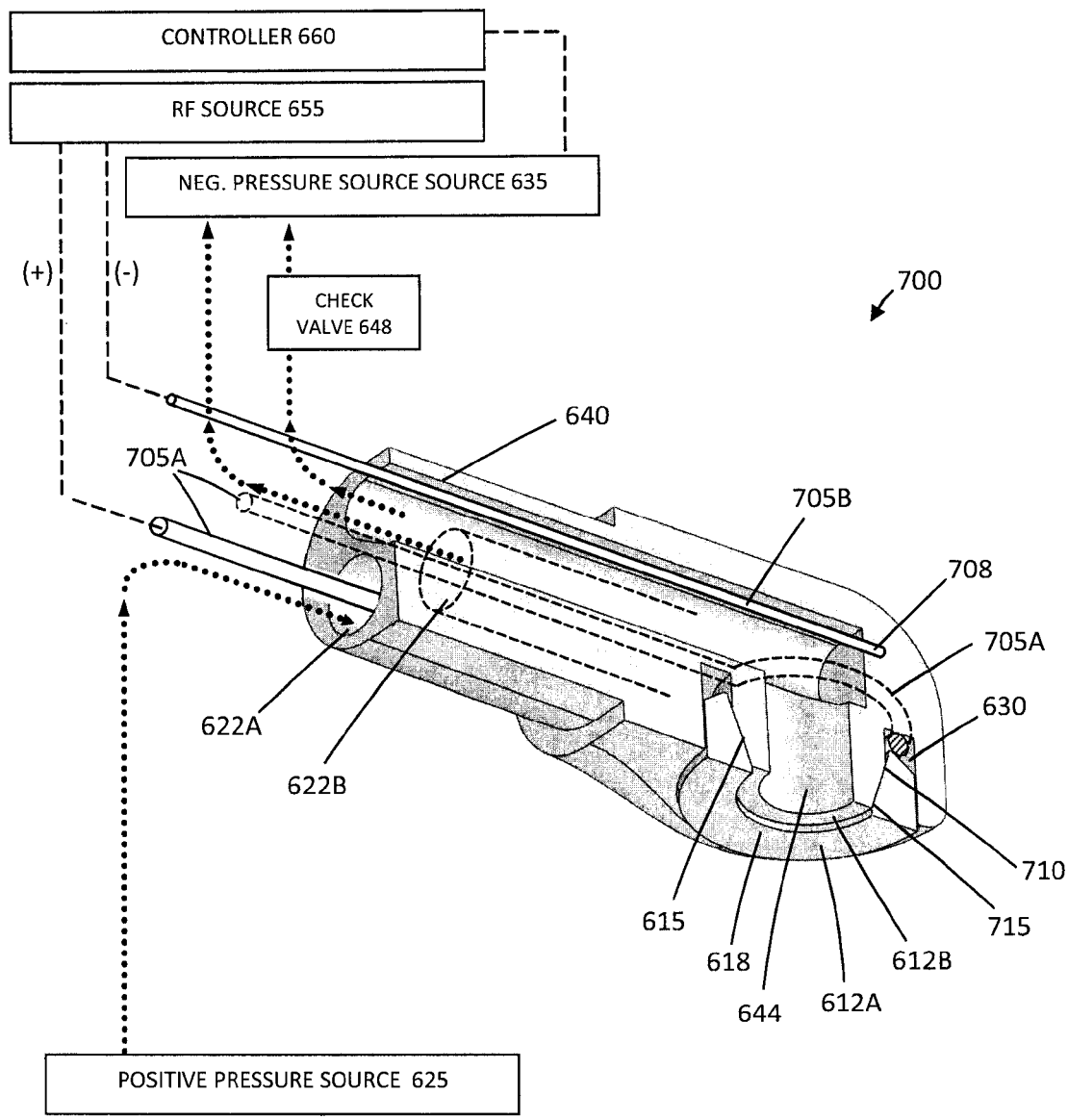
FIG. 20 is a sectional view of another working end variation similar to that of FIGS. 16A-18B with a different annular interface between dielectric bodies configured for plasma formation therein and plasma propagation therethrough together with an alternative electrode arrangement.

FIG. 20 illustrates another working end 700 embodiment that is similar to that of FIGS. 16A-18B except that the opposing polarity first and second electrodes 705A and 705B have a different configuration—still positioned within the interior channels of the working end 700. As can be seen in FIG. 20, the inflow and outflow channels 622A and 622B are similar to previous embodiments. The working end 700 further has a fluid extraction channel 640 as described previously. In one variation, the working end 700 has a looped wire first polarity electrode 705A extending through the working end through first inflow channel 622B, around looped channel portion 630 adjacent interface 615 and extending partly through second outflow channel 622B. In the working end 700 of FIG. 20, both the first and second electrodes 705A and 705B are round wires with large surface areas which enhances RF current flow in the fluid environment. This electrode configuration provides an increased surface area to the electrode and extends such an electrode surface around the region of plasma ignition which together with the absence of sharp edges can enhance the uniformity of the plasma generation in the interface 615. The electrode 705A can have any suitable diameter ranging from about 0.005" to 0.10". Similarly, the second polarity electrode 705B is configured to have a substantial exposed surface with a length, for example, ranging from 2 mm to 20 mm (and diameter of about 0.005" to 0.10") in the tissue-extraction channel 640. The distal end 708 of the electrode 705A is embedded and sealed into ceramic housing 614 to prevent any sharp electrode edges exposed to the channel 640.

As can be understood from FIG. 20, the RF current paths CP between the first and second polarity electrodes 705A and 705B extends through the interface 615 between the ceramic bodies 612A and 612Bt as described previously. In another aspect of the invention, still referring to FIG. 20, the interface 615 has a greatly increased surface area compared to previous embodiments. It can be seen in FIG. 20 that a tapered annual interface 615 is provided between the dielectric bodies 612A and 612B which after assembly comprises an extremely small gap. In one embodiment, the interface is dimensioned to be sufficiently fluid-tight to prevent liquid flow therethrough and will only permit current flows and plasma propagation therethrough. In this embodiment, the tapered interface or taper lock between the first and second dielectric bodies 612A and 612B is provided by a predetermined surface roughness that is fabricated on either or both dielectric bodies 612A and 612B at either side of the interface 615. In other words, the first and second dielectric bodies 612A and 612B are wedged together tightly with a micron or sub-micron dimensioned gap between the surface finishes of the mating dielectric bodies.

In one embodiment, the interface 615 is annular as shown in FIG. 20 and extends between a first interior periphery 710 of the interface 615 and a second exterior periphery 715 of the interface wherein the mean dimension between the inner and outer peripheries ranges from 0.005" to 0.25". Although the variation of FIG. 20 illustrates an annular interface 615, the scope of the invention includes any interface configuration such as a linear configuration, an oval configuration, any elongated configuration, or a polygonal or star-shaped configuration. The total area of such an interface 615 can be from 0.01 mm² to 10 mm².

In general, a method of ablating tissue corresponding to the invention comprises providing an electrosurgical working end with an interior chamber communicating with a working surface through a space that is sufficiently fluid-tight to prevent liquid flow therethrough but permit plasma propagation therethrough, igniting a plasma in the gap utilizing first and second opposing polarity electrodes positioned on either side of the gap, and controlling propagation of the plasma through the gap to interface with tissue. In one aspect of the invention, the plasma propagation is controlled by controlling pressure interior of the gap. In another aspect of the invention, the plasma propagation is controlled by controlling the dimensions of said gap which can comprised the width or cross section of the gap and/or the dimension between the inner and outer peripheries of the gap.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

What is claimed is:

1. A system for treating a target tissue, said system comprising:
a probe having an interior space and a working end with a working surface;
a gap in a wall of the working end, wherein the gap has a spacing which is sufficiently fluid tight to inhibit liquid flow but permit plasma propagation therethrough;
means for igniting a plasma within the interior space, wherein the plasma propagates outwardly from the interior space through the gap to the working surface.

2. A system as in claim 1, wherein the means for igniting the plasma comprises means for igniting a conductive media passing through the gap.

3. A system as in claim 2, wherein the spacing of the gap is defined by an interior periphery and an exterior periphery.

4. A system as in claim 3, wherein a mean dimension between said interior and exterior peripheries of the interface is from 0.005 inch to 0.25 inch.

5. A system as in claim 3, wherein the total area of the interface is from 0.01 mm² to 10 mm².

6. A system as in claim 3, wherein the gap has an annular configuration, a linear configuration, an oval configuration, an elongated configuration, or a star-shaped configuration.

7. A system as in claim 3, wherein the means for igniting the plasma applies electrical energy to the conductive media from opposite polarity electrodes.

8. A system as in claim 7, wherein the means for igniting the plasma comprises a first polarity electrode is disposed in proximity to the inner periphery.

9. A system as in claim 8, wherein the first polarity electrode is disposed in a fluid channel in communication with said inner periphery.

10. A system as in claim 9, wherein the means for igniting the plasma further comprises a second polarity electrode in the working end in potential fluid communication with said exterior periphery.

11. A system as in claim 2, further comprising means for controlling a rate of propagation through the gap.

12. A system as in claim 11, wherein the means for controlling a rate of propagation through the gap controls a dimension of said gap.

13. A system as in claim 12, wherein the means for controlling a rate of propagation through the gap controls a width of said gap.

14. A system as in claim 13, wherein the means for controlling a rate of propagation through the gap controls a dimension of said gap between a plasma ignition region and the working surface.

15. A system as in claim 11, wherein the means for controlling a rate of propagation through the gap varies a pressure of the conductive media in the interior space.

16. A system as in claim 15, wherein the conductive media is introduced into the interior space under a controlled pressure.

17. A system as in claim 15, wherein the conductive media is removed from the interior space under a controlled negative pressure.

18. A system as in claim 1, wherein the means for igniting a plasma within the interior space establishes a continuous loop flow of a conductive media through the interior space wherein a portion of the conductive media is ignited within the interior space and a remainder exits the interior space.

19. A system as in claim 18, wherein the conductive media enters the interior space through an inlet flow channel in the probe, the remainder exits through an outlet flow channel in the probe, and the plasma exits through one or more gaps in the working end.

20. A system as in claim 19, wherein a propagation rate of the plasma is controlled by varying the inlet pressure of conductive media in the inlet channel and an outlet pressure of conductive media in the outlet channel.

21. A system as in claim 19, wherein the plasma is ignited by passing currents through opposed polarity electrodes in the interior space.

22. A system as in claim 21, wherein the interior space comprises a channel transition zone between the inlet and outlet channels.

23. A system as in claim 22, wherein the channel transition zone comprises a flow restriction.

24. A system as in claim 23, wherein the plasma is ignited at said flow restriction.

* * * * *